(12) United States Patent  
Khandros et al.

(10) Patent No.: US 11,192,107 B2  
(45) Date of Patent: Dec. 7, 2021

(54) DEP FORCE CONTROL AND ELECTROWETTING CONTROL IN DIFFERENT SECTIONS OF THE SAME MICROFLUIDIC APPARATUS

(71) Applicant: Berkeley Lights, Inc., Emeryville, CA (US)

(72) Inventors: Igor Y. Khandros, Orinda, CA (US); J. Tanner Nevill, El Cerrito, CA (US); Steven W. Short, Pleasanton, CA (US); Ming C. Wu, Moraga, CA (US)

(73) Assignee: Berkeley Lights, Inc., Emeryville, CA (US)

( * ) Notice: Subject to any disclaimer, the term of this patent is extended or adjusted under 35 U.S.C. 154(b) by 224 days.

(21) Appl. No.: 15/306,355

(22) PCT Filed: Apr. 25, 2015

(86) PCT No.: PCT/US2015/027679  
§ 371 (c)(1),  
(2) Date: Oct. 24, 2016

(87) PCT Pub. No.: WO2015/164846  
PCT Pub. Date: Oct. 29, 2015

(65) Prior Publication Data  
US 2017/0043343 A1 Feb. 16, 2017

Related U.S. Application Data

(63) Continuation-in-part of application No. 14/262,140, filed on Apr. 25, 2014, now abandoned.

(51) Int. Cl.  
*B03C 5/00* (2006.01)  
*B01L 3/00* (2006.01)  
(Continued)

(52) U.S. Cl.  
CPC ... *B01L 3/502761* (2013.01); *B01L 3/502784* (2013.01); *B03C 5/005* (2013.01);  
(Continued)

(58) Field of Classification Search  
CPC ............. B01L 3/502784; B03C 5/005–028  
See application file for complete search history.

(56) References Cited

U.S. PATENT DOCUMENTS 4,390,403 A * 6/1983 Batchelder ............ B03C 5/022  
204/547  
5,814,200 A 9/1998 Pethig  
(Continued)

FOREIGN PATENT DOCUMENTS

CN 101275114 A 10/2008  
EP 2570188 3/2013  
(Continued)

OTHER PUBLICATIONS

Fan et al. (Lab Chip, 8, 1325-1331) (Year: 2008).*  
(Continued)

*Primary Examiner* — Alexander S Noguerola  
(74) *Attorney, Agent, or Firm* — Kenneth E. Horton; Barnes & Thornburg LLP

(57) ABSTRACT

A microfluidic apparatus can comprise a dielectrophoresis (DEP) configured section for holding a first liquid medium and selectively inducing net DEP forces in the first liquid medium. The microfluidic apparatus can also comprise an electrowetting (EW) configured section for holding a second liquid medium on an electrowetting surface and selectively changing an effective wetting property of the electrowetting surface. The DEP configured section can be utilized to select and move a micro-object in the first liquid medium. The EW configured section can be utilized to pull a droplet of the first liquid medium into the second liquid medium.

25 Claims, 21 Drawing Sheets

(51) Int. Cl.
  *C12M 3/06* (2006.01)
  *C12M 1/12* (2006.01)
  *B03C 5/02* (2006.01)
  *C12M 1/02* (2006.01)
  *C12M 1/00* (2006.01)
  *C12M 1/42* (2006.01)

(52) U.S. Cl.
  CPC ............ *B03C 5/026* (2013.01); *C12M 23/16* (2013.01); *C12M 23/20* (2013.01); *C12M 25/16* (2013.01); *C12M 27/00* (2013.01); *C12M 35/02* (2013.01); *B01L 2200/0647* (2013.01); *B01L 2200/0668* (2013.01); *B01L 2200/0673* (2013.01); *B01L 2300/0816* (2013.01); *B01L 2300/0819* (2013.01); *B01L 2300/0864* (2013.01); *B01L 2400/0424* (2013.01); *B01L 2400/0427* (2013.01); *B03C 2201/26* (2013.01)

(56) References Cited

U.S. PATENT DOCUMENTS

| | | | |
|---|---|---|---|
| 6,294,063 | B1 | 9/2001 | Becker |
| 6,565,727 | B1 | 5/2003 | Shenderov |
| 6,773,566 | B2 | 8/2004 | Shenderov |
| 6,942,776 | B2 | 9/2005 | Medoro |
| 6,958,132 | B2 | 10/2005 | Chiou et al. |
| 7,090,759 | B1 | 8/2006 | Seul |
| 7,815,871 | B2 * | 10/2010 | Pamula ............... B41J 2/125 422/404 |
| 8,228,657 | B2 | 7/2012 | Jones et al. |
| 8,864,972 | B2 * | 10/2014 | Yamakawa ............ B01D 57/02 204/547 |
| 9,091,649 | B2 * | 7/2015 | Pollack ............ B01L 3/502792 |
| 9,188,615 | B2 * | 11/2015 | Sturmer ............... G01N 27/048 |
| 9,201,042 | B2 * | 12/2015 | Bhattacharya ...... B01F 13/0071 |
| 2003/0008364 | A1 | 1/2003 | Wang et al. |
| 2003/0047456 | A1 | 3/2003 | Medoro |
| 2003/0205632 | A1 | 11/2003 | Kim et al. |
| 2003/0224528 | A1 | 12/2003 | Chiou |
| 2004/0072278 | A1 | 4/2004 | Chou et al. |
| 2004/0191789 | A1 | 9/2004 | Manaresi |
| 2004/0197905 | A1 | 10/2004 | Hafeman |
| 2005/0112548 | A1 | 5/2005 | Segawa et al. |
| 2005/0129581 | A1 | 6/2005 | McBride et al. |
| 2005/0164402 | A1 | 7/2005 | Belisle et al. |
| 2005/0175981 | A1 | 11/2005 | Voldman |
| 2006/0091015 | A1 | 5/2006 | Lau |
| 2006/0154361 | A1 | 7/2006 | Wikswo et al. |
| 2006/0186048 | A1 * | 8/2006 | Tan ....................... G01N 1/4055 210/656 |
| 2007/0023292 | A1 | 2/2007 | Kim |
| 2007/0095669 | A1 | 3/2007 | Lau |
| 2007/0148763 | A1 | 6/2007 | Huh et al. |
| 2007/0183934 | A1 | 9/2007 | Diercks |
| 2007/0242105 | A1 | 10/2007 | Srinivasan |
| 2007/0243634 | A1 | 10/2007 | Pamula et al. |
| 2008/0038810 | A1 | 2/2008 | Pollack |
| 2008/0169195 | A1 | 7/2008 | Jones et al. |
| 2008/0223721 | A1 | 9/2008 | Cohen et al. |
| 2008/0274513 | A1 | 11/2008 | Shenderov |
| 2008/0302732 | A1 | 12/2008 | Soh et al. |
| 2009/0023608 | A1 | 1/2009 | Hung et al. |
| 2009/0170186 | A1 | 7/2009 | Wu |
| 2009/0192044 | A1 | 7/2009 | Fouillet |
| 2010/0000620 | A1 | 1/2010 | Fouillet |
| 2010/0101960 | A1 | 4/2010 | Ohta |
| 2010/0000366 | A1 | 7/2010 | Lee |
| 2010/0181195 | A1 | 7/2010 | Garcia Tello |
| 2010/0219076 | A1 | 9/2010 | Yamakawa |
| 2010/0273681 | A1 | 10/2010 | Cerrina et al. |
| 2011/0053151 | A1 | 3/2011 | Hansen et al. |
| 2011/0086377 | A1 * | 4/2011 | Thwar ............ B01L 3/502761 435/29 |
| 2011/0095201 | A1 | 4/2011 | Stolowitz |
| 2011/0117634 | A1 | 5/2011 | Halamish |
| 2011/0143964 | A1 | 6/2011 | Zhou et al. |
| 2011/0262906 | A1 | 10/2011 | Dimov et al. |
| 2012/0009671 | A1 | 1/2012 | Hansen et al. |
| 2012/0015347 | A1 | 1/2012 | Singhal et al. |
| 2012/0024708 | A1 | 2/2012 | Chiou |
| 2012/0118740 | A1 | 5/2012 | Garcia et al. |
| 2012/0156675 | A1 | 6/2012 | Lueerssen et al. |
| 2012/0325665 | A1 | 12/2012 | Chiou |
| 2013/0026040 | A1 | 1/2013 | Cheng et al. |
| 2013/0062205 | A1 | 3/2013 | Hadwen et al. |
| 2013/0061021 | A1 | 3/2013 | Bocchi |
| 2013/0171628 | A1 | 4/2013 | DiCarlo et al. |
| 2013/0105319 | A1 | 5/2013 | Bhattacharya et al. |
| 2013/0115606 | A1 | 5/2013 | Hansen et al. |
| 2013/0118905 | A1 | 5/2013 | Morimoto |
| 2013/0130232 | A1 | 5/2013 | Weibel et al. |
| 2013/0190212 | A1 | 7/2013 | Handique |
| 2013/0204076 | A1 | 8/2013 | Han |
| 2013/0206597 | A1 | 8/2013 | Wang et al. |
| 2013/0288254 | A1 | 10/2013 | Pollack et al. |
| 2014/0016176 | A1 * | 1/2014 | Kodani ............ B01L 3/502707 359/290 |
| 2014/0116881 | A1 | 1/2014 | Chapman |
| 2014/0124370 | A1 | 5/2014 | Short |
| 2014/0378339 | A1 | 12/2014 | Lammertyn et al. |
| 2015/0018226 | A1 | 1/2015 | Hansen et al. |
| 2015/0107995 | A1 | 4/2015 | Sista et al. |
| 2015/0151298 | A1 | 6/2015 | Hobbs |
| 2015/0151307 | A1 | 6/2015 | Breinlinger |
| 2015/0165436 | A1 | 6/2015 | Chapman |
| 2015/0259754 | A1 * | 9/2015 | Kaier ............... B01L 3/502792 506/9 |
| 2015/0306598 | A1 | 10/2015 | Khandros et al. |
| 2015/0306599 | A1 | 10/2015 | Khandros |
| 2016/0158748 | A1 | 6/2016 | Wu et al. |
| 2016/0184821 | A1 | 6/2016 | Hobbs et al. |
| 2016/0199837 | A1 | 7/2016 | Breinlinger et al. |
| 2016/0252495 | A1 | 9/2016 | Ricicova et al. |
| 2016/0312165 | A1 | 10/2016 | Lowe, Jr. et al. |
| 2018/0298318 | A1 | 10/2018 | Kurz et al. |
| 2019/0240665 | A1 | 8/2019 | Lionberger et al. |

FOREIGN PATENT DOCUMENTS

| | | |
|---|---|---|
| JP | 2006220606 A | 8/2006 |
| JP | 2007-537729 A | 12/2007 |
| JP | 2011523064 A | 8/2011 |
| JP | 2012034641 A | 2/2012 |
| JP | 2013-078758 A | 5/2013 |
| JP | 2017-519618 A | 7/2017 |
| KR | 20100008222 A | 1/2010 |
| KR | 20120045886 A | 5/2012 |
| KR | 10-2012-0066100 A | 6/2012 |
| KR | 2012006610 | 6/2012 |
| KR | 20120066100 | 6/2012 |
| WO | 2002008702 A2 | 11/2002 |
| WO | 2004012848 A2 | 2/2004 |
| WO | 2004089810 A2 | 10/2004 |
| WO | 2005100541 A2 | 10/2005 |
| WO | 2007008609 A2 | 1/2007 |
| WO | 2007024701 A2 | 3/2007 |
| WO | 2007120241 A2 | 10/2007 |
| WO | 2008119066 A1 | 10/2008 |
| WO | 2009130694 A2 | 10/2009 |
| WO | 2009149467 A2 | 12/2009 |
| WO | 2010040851 A2 | 4/2010 |
| WO | 2010115167 A2 | 10/2010 |
| WO | 2010147078 A1 | 12/2010 |
| WO | 20100147078 | 12/2010 |
| WO | 2011160430 A1 | 12/2011 |
| WO | 2012037030 A2 | 3/2012 |
| WO | 2012072823 A1 | 6/2012 |
| WO | 2012162779 A1 | 12/2012 |
| WO | 2013019491 A1 | 2/2013 |
| WO | 2014036915 | 3/2014 |

(56) References Cited

FOREIGN PATENT DOCUMENTS

WO         2015164846 A1     10/2015
WO         2015164847        10/2015

OTHER PUBLICATIONS

Prakash et al., "Droplet Microfluidic Chip Based Nucleic Acid Amplification and real-Time Detection of Influenza Viruses," Journal of The Electrochemical Society, 161, (2) B3083-B3093 (2014) (JES Focus Issue on Microfluidics, MEMS/NEMS, Sensors and Devices), published Dec. 27, 2013 (Year: 2013).*

Chiou et al., Massively parallel manipulation of single cells and microparticles using optical images, Nature 436:370-73 (2005).

Valley et al., A unified platform for optoelectrowetting and optoelectronic tweezers, Lab on a Chip 11:1292-97 (2011).

KIPO computer-generated English language translation of KR 10-2012-0066100 Gwang-Seok Yang, patent published Jun. 22, 2012.

Fan et al. Cross-scale electric manipulation of cells and droplet by frequency-modulated dielectrophoresis and electrowetting, Lab Chip, 2008, 8, 1325-1331.

International Search Report and Written Opinion for PCT Application Serial No. PCT/2015/027680 (dated Jun. 29, 2015), 9 pages.

International Search Report and Written Opinion for PCT Application Serial No. PCT/2015/027679 (dated Jul. 27, 2015), 11 pages.

Huang et al., Digital Microfluidic Dynamic Culture of Mammalian Embryos on an Electrowetting on Dielectric (EWOD) Chip, PLOS one 10(5):e0124196 (2015).

Chiou_Dissertation_UC Berkeley "Massively Parallel Optical Manipulation of Single Cells, Micro- and Nano-particles on Optoelectronic Devices" 2005.

Chung et al., Imaging Single-Cell Signaling Dynamics with a Deterministic High-Density Single-Cell Trap Array, Anal. Chem. 83(18):7044-7052 (2011).

Fuchs et al., "Electronic sorting and recovery of single live cells from microlitre sized samples" Lab on a Chip 6:121-26 (2006).

Hsu, Hy et al., "Sorting of Differentiated Neurons Using Phototransistor-Based Optoelectronic Tweezers for Cell Replacement Therapy of Neurodegenerative Diseases", Transducers 2009, Denver, CO USA Jun. 2009, download dated Nov. 23, 2009 from IEEE Xplore, 4 pages.

Hung et al., Continuous Perfusion Microfluidic Cell Culture Array for High-Throughput Cell-Based Assays, Biotech and Bioengineering 89(1): 1-8 (2004). Dec. 3, 2004.

Iliescu et al., Continuous Field-Flow Separation of Particle Populations in a Dielectrophoretic Chip with Three Dimensional Electrodes, Applied Physics Letters 90:234104 (2007).

Nevill et al., Integrated microfluidic cell culture and lysis on a chip, Lab on a Chip 7:1689-95 (2007).

Pei et al., Light-Actuated Digital Microfluidics for Large-Scale, Parallel Manipulation of Arbitrarily Sized Droplets, 2010 IEEE 23rd Intl. Conf. on MEMS, pp. 252-255.

Somaweera H. et al., Generation of a Chemical Gradient Across an Array of 256 Cell Cultures in a Single Chip. Analyst, Oct. 7, 2013, vol. 138, No. 19, pp. 5566-5571.

Valley et al., An Integrated Platform for Light-Induced Dielectro-Phoresis and Electrowetting, International Conference on Miniaturized Systems for Chemistry and Life Sciences (2010).

Valley et al., Optoelectronic Tweezers as a Tool for Parallel Single-Cell Manipulation and Simulation, IEEE Transactions on Biomedical Circuits and Systems, vol. 3, No. 6 (Dec. 2009), pp. 424-431.

Xu, Guoling et al,. Recent Trends in Dielectrophoresis, Informacije MIDEM, 2010, vol. 40, Issue No. 4, pp. 253-262.

Yi et al., "Microfluidics technology for manipulation and analysis of biological cells," Analytica Chimica Acta 560 (2006), pp. 1-23.

* cited by examiner

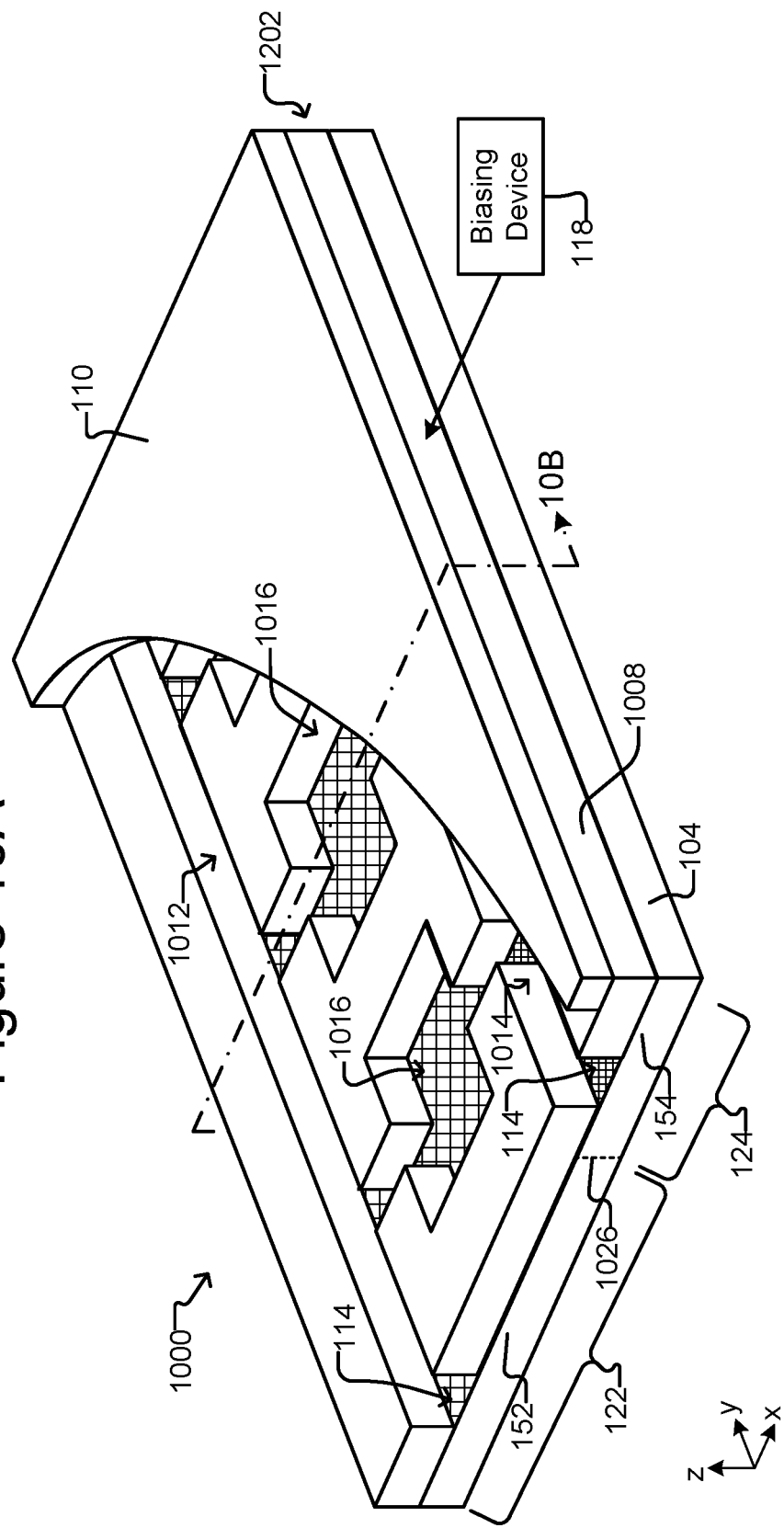

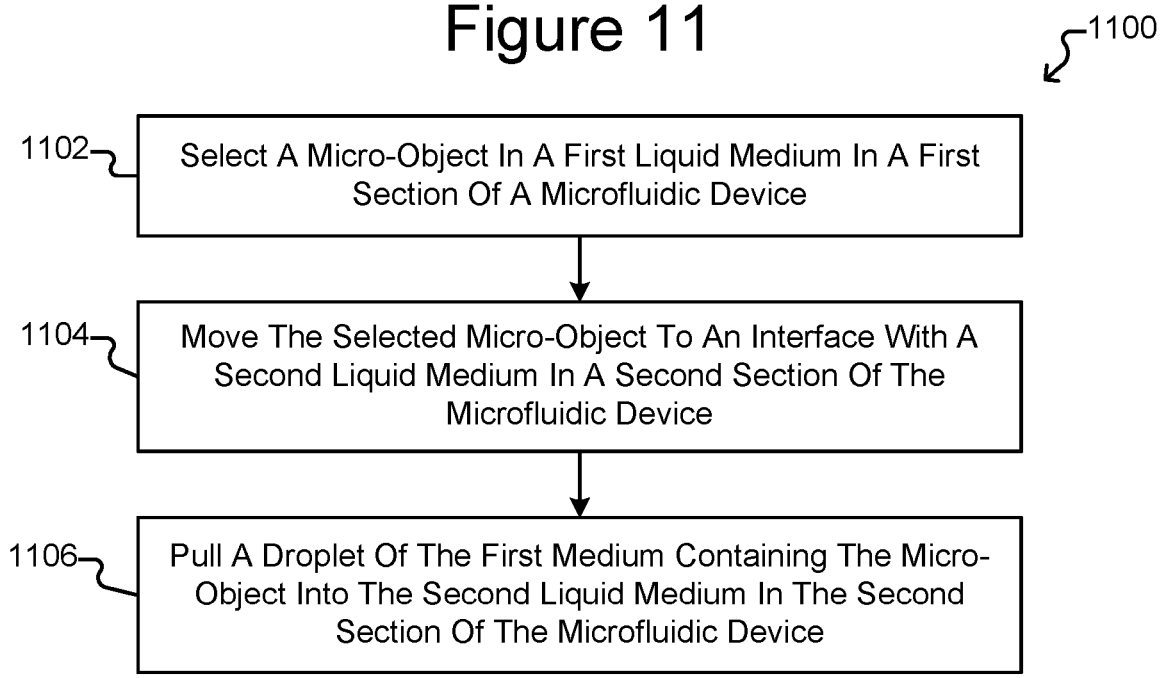
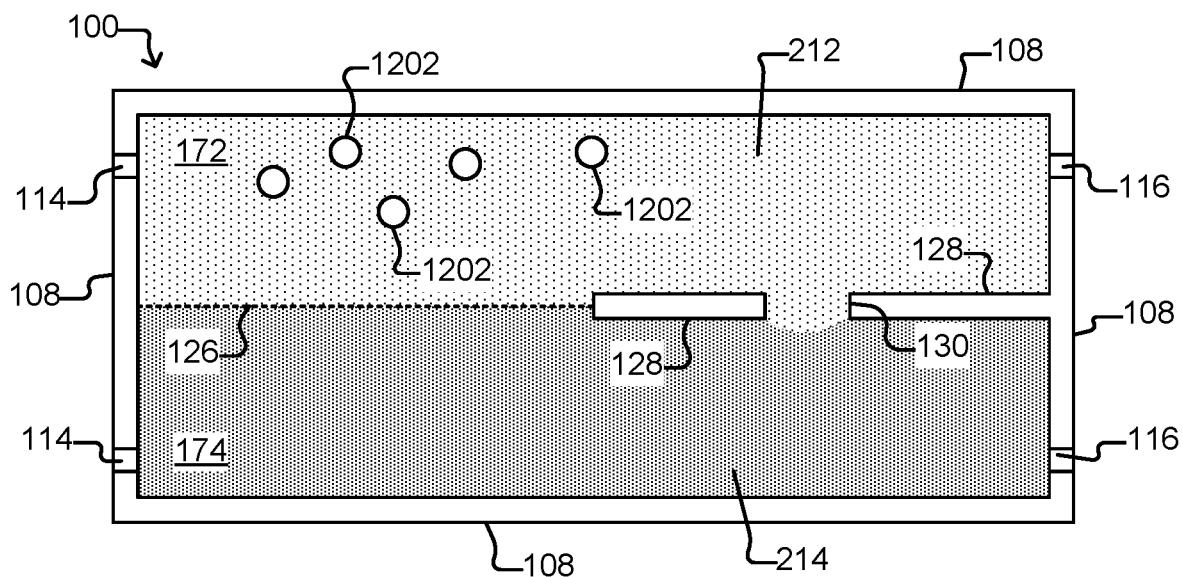

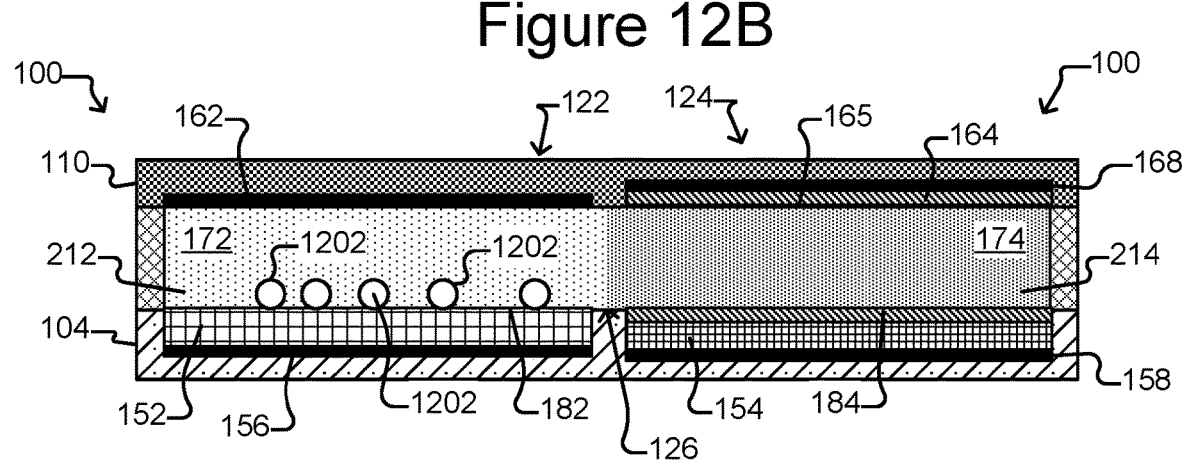
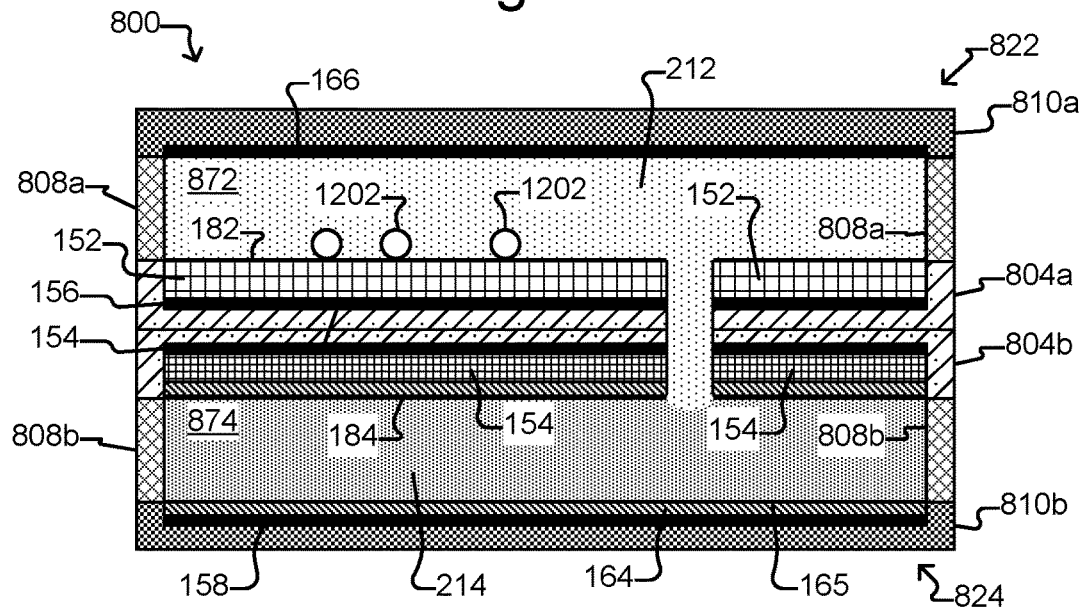

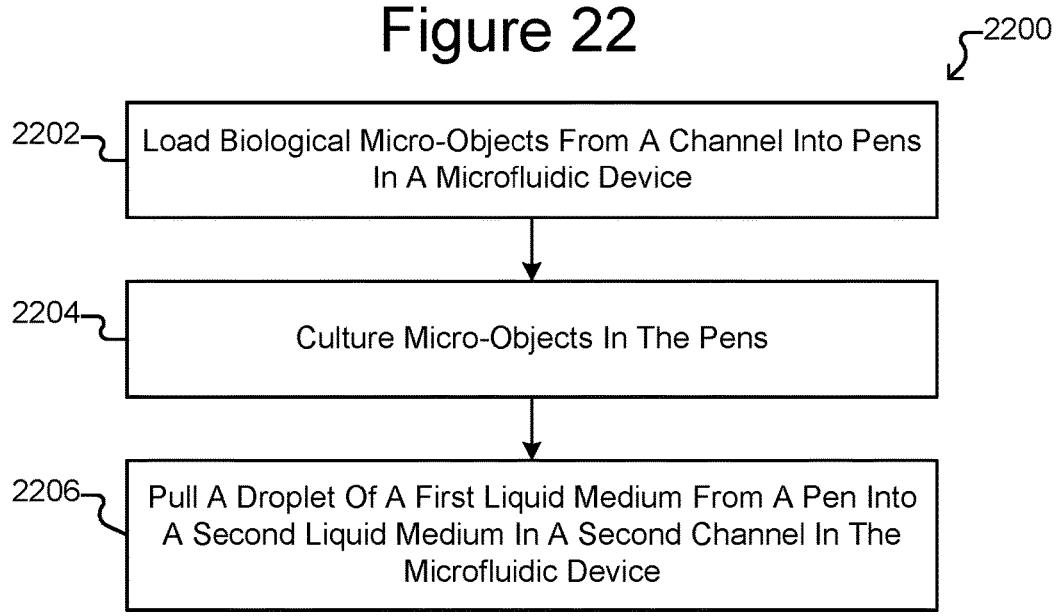
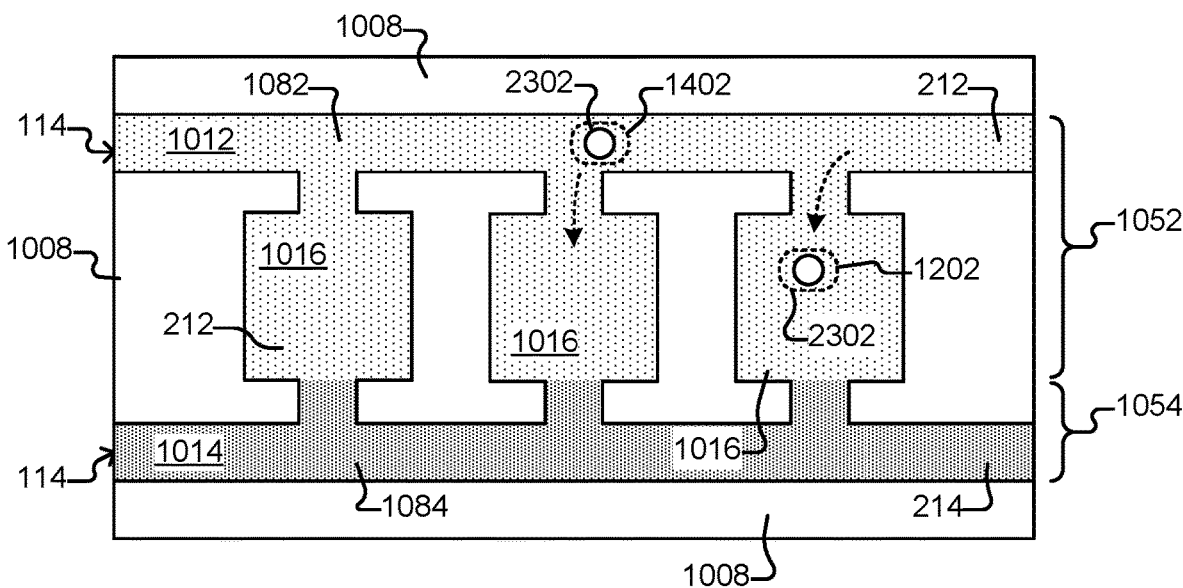

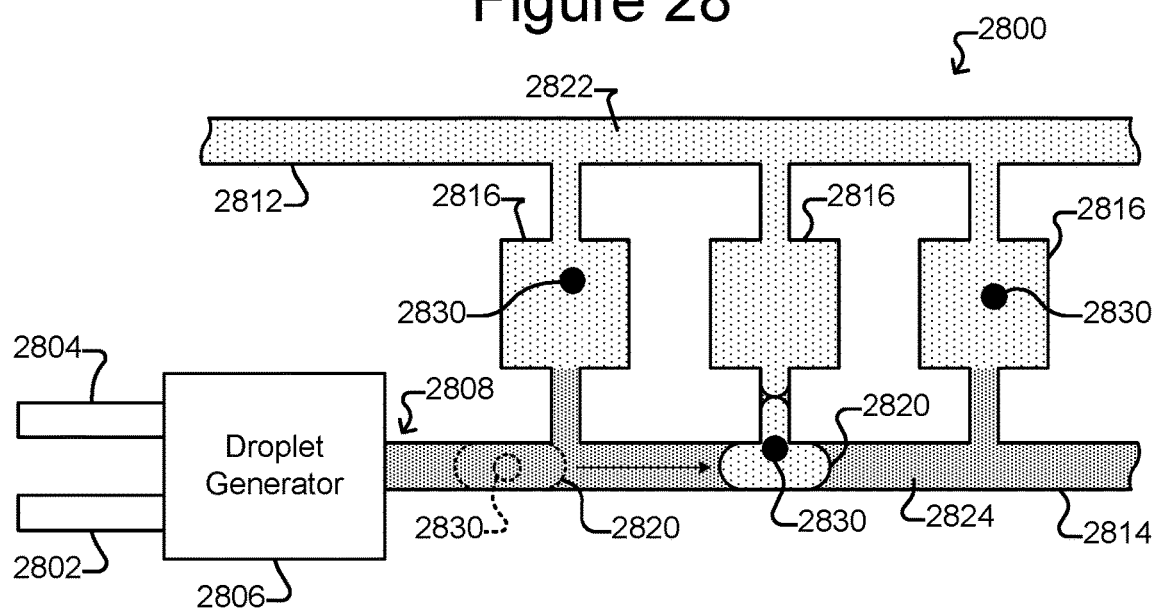
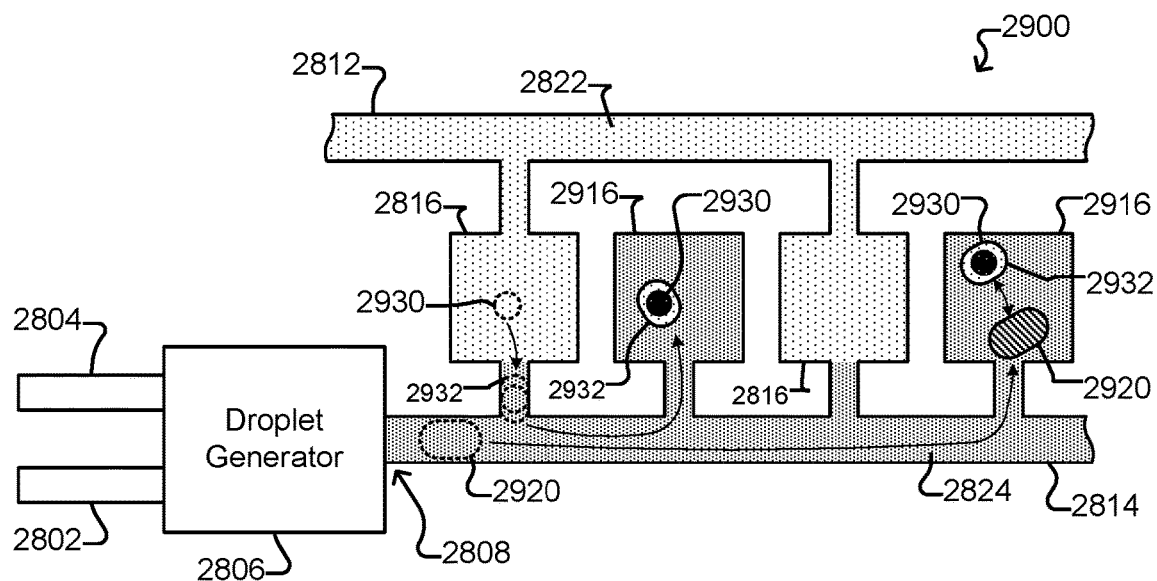

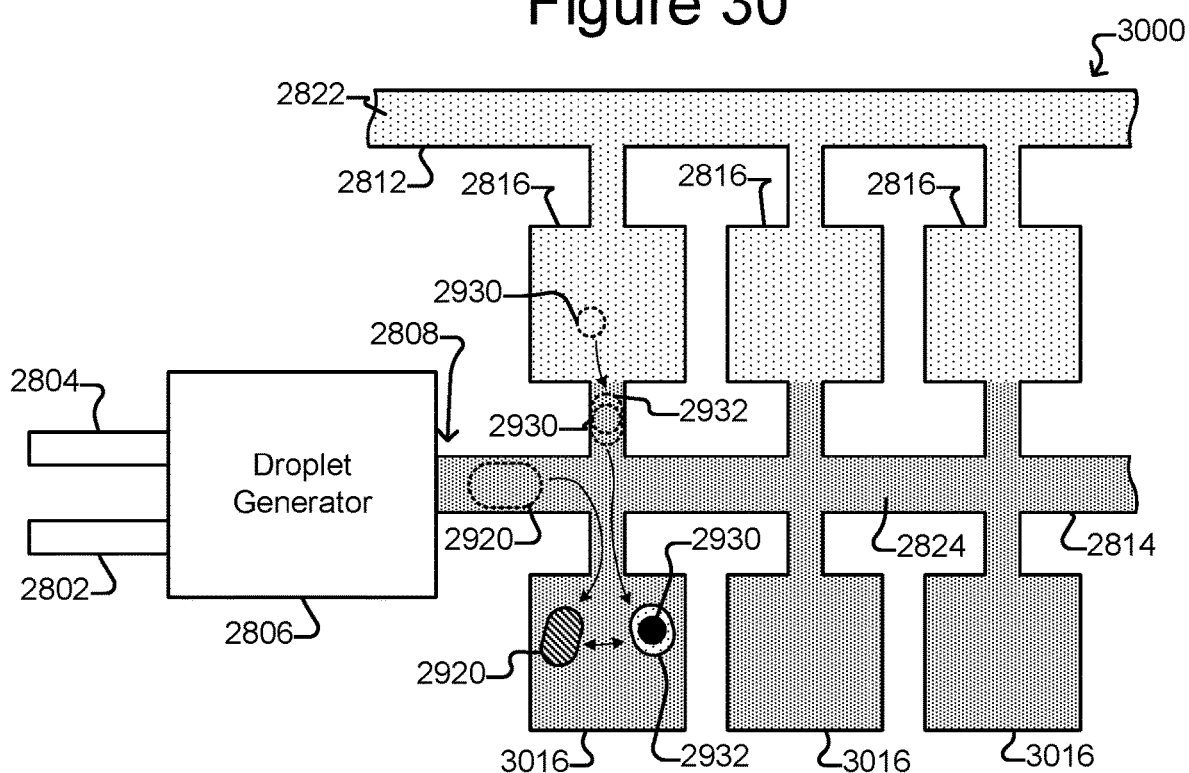
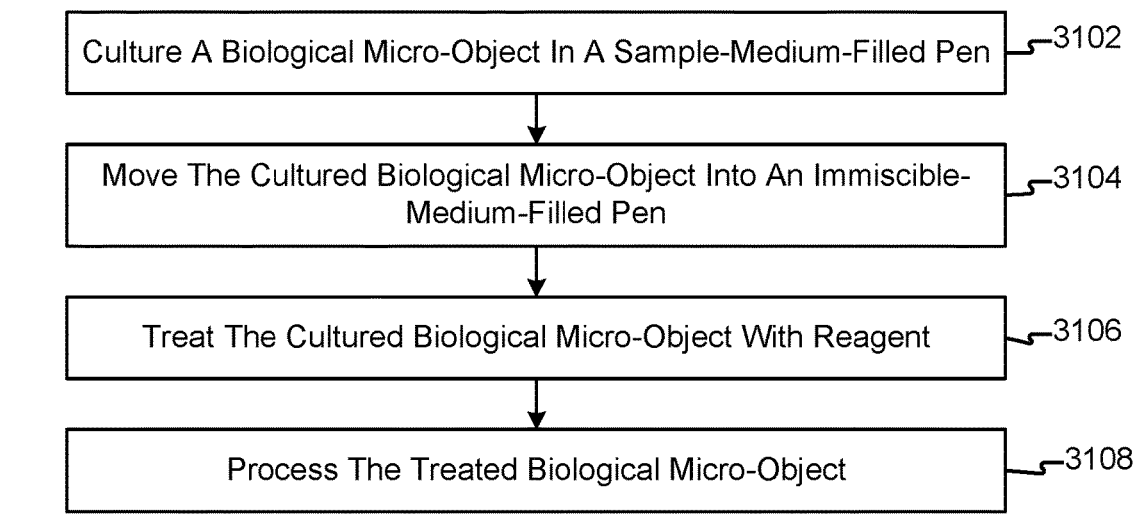

DEP FORCE CONTROL AND ELECTROWETTING CONTROL IN DIFFERENT SECTIONS OF THE SAME MICROFLUIDIC APPARATUS

CROSS REFERENCE TO RELATED APPLICATION(S)

This application claims priority to U.S. patent application Ser. No. 14/262,140, filed Apr. 25, 2014, the entire contents of which are incorporated herein by reference in their entirety.

BACKGROUND

Micro-objects, such as biological cells, can be processed in microfluidic apparatuses. For example, micro-objects suspended in a liquid in a microfluidic apparatus can be sorted, selected, and moved in the microfluidic apparatus. The liquid can also be manipulated in the device. Embodiments of the present invention are directed to improvements in selectively generating net DEP forces in a first section of a microfluidic apparatus and changing an effective wetting property of an electrowetting surface in another section of the microfluidic apparatus.

SUMMARY

In some embodiments, an apparatus can include an enclosure, a dielectrophoresis (DEP) configuration, and an electrowetting (EW) configuration. The enclosure can comprise a first surface and an electrowetting surface. The DEP configuration can be configured to selectively induce net DEP forces in a first liquid medium disposed on the first surface, and the EW configuration can be configured to selectively change an effective wetting property of the electrowetting surface.

In some embodiments, a process of operating a fluidic apparatus can include inducing a net DEP force on a micro-object in a first liquid medium on a first surface in a first section of the apparatus. The process can also include changing an effective wetting property of a region of an electrowetting surface on which a second liquid medium is disposed in a second section of the apparatus.

In some embodiments, an apparatus can comprise an enclosure and a boundary. The enclosure can be configured to hold a first liquid medium disposed on a first surface in a first section of the enclosure and a second liquid medium disposed on an electrowetting surface in a second section of the enclosure. The boundary can be between the first section and the second section of the enclosure. The first section of the enclosure can comprise a DEP configuration configured to induce selectively net DEP forces in the first liquid medium sufficiently to capture and move, relative to the first surface, micro-objects in the first liquid medium in the first section of the enclosure, while the first section is connected to a biasing device. The second section of the enclosure can comprise an EW configuration configured to change selectively an effective wetting characteristic of regions of the electrowetting surface sufficiently to move a liquid droplet within the second medium in the second section of the enclosure, while the second section is connected to a biasing device.

In some embodiments, a process of operating a fluidic apparatus can include drawing a droplet of a first liquid medium disposed on a first surface in a first section of an enclosure into a second medium disposed on an electrowetting surface in a second section of the enclosure. The foregoing drawing can include changing an electroeffective wetting characteristic of a region of the electrowetting surface at a boundary with the first surface and thereby induce a force at the boundary that is sufficient to draw a droplet across the boundary and into the second liquid medium.

BRIEF DESCRIPTION OF THE DRAWINGS

FIG. 10A is a perspective view of an example of a microfluidic apparatus comprising a DEP configuration for manipulating micro-objects in a first section of the device and an EW configuration for manipulating droplets of a liquid medium on an electrowetting surface in a second section of the device according to some embodiments of the invention.

FIG. 11 is an example of a process for moving a micro-object from a first liquid medium in a first section of a microfluidic apparatus into a second liquid medium in a second section of the microfluidic apparatus according to some embodiments of the invention.

FIGS. 12A-21 show examples of performance of the process of FIG. 11 according to some embodiments of the invention.

FIG. 22 is an example of a process for culturing biological micro-objects in a microfluidic apparatus configured to hold multiple different liquid media according to some embodiments of the invention.

FIGS. 23-26 illustrate an example of performance of the process of FIG. 22 according to some embodiments of the invention.

FIG. 28 illustrates an example in which a droplet generator is used to produce droplets in a channel of a microfluidic circuit according to some embodiments of the invention.

FIGS. 29 and 30 show variations of the microfluidic circuit of FIG. 28.

FIG. 31 is an example of a process for analyzing biological micro-objects in the microfluidic circuits of FIGS. 28-30.

DETAILED DESCRIPTION OF EXEMPLARY EMBODIMENTS

Figure 1A:
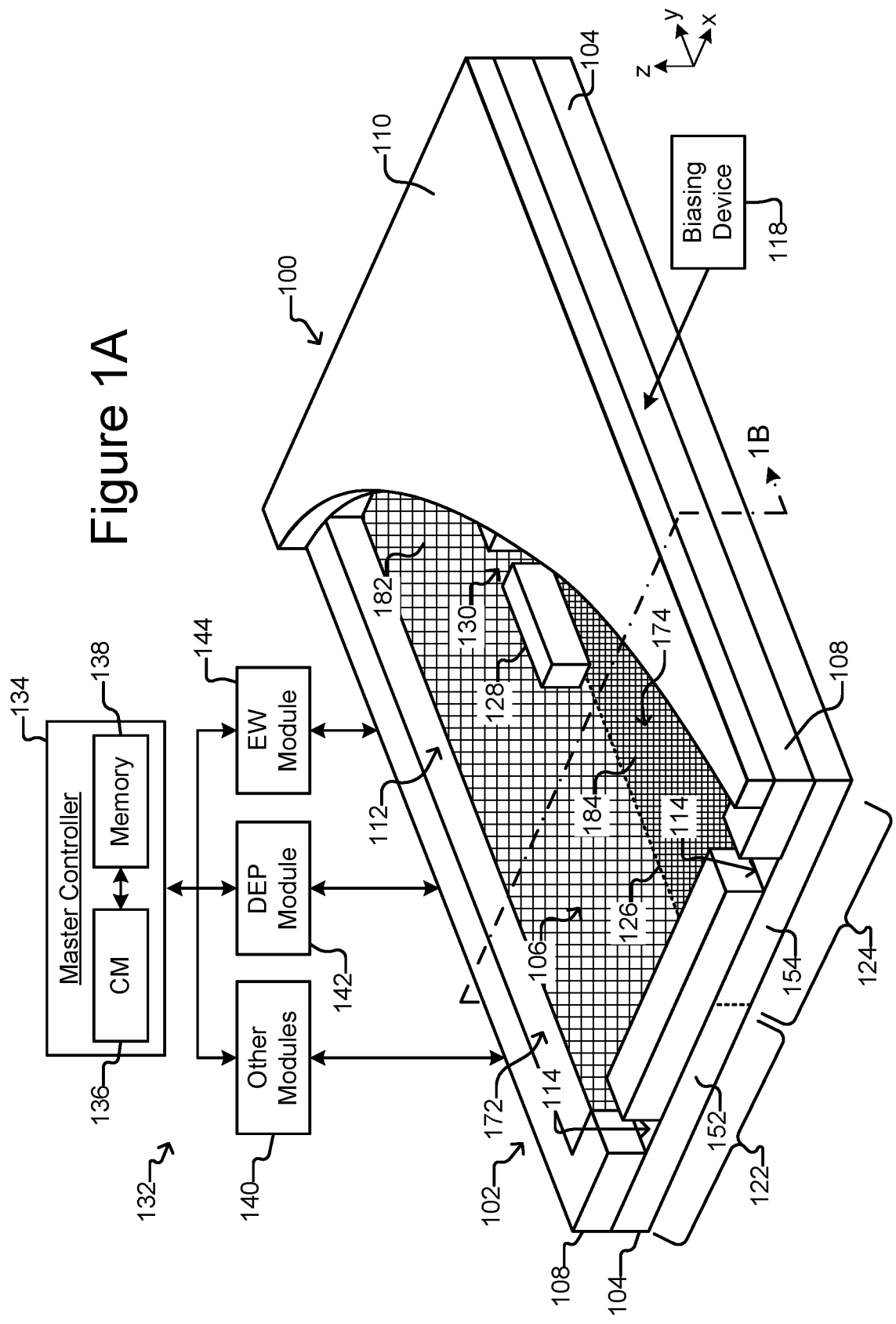
FIG. 1A is a perspective view of a microfluidic apparatus comprising sections for holding different liquid medium, inducing net dielectrophoresis (DEP) forces in one section and controlling an effective electrowetting property of a surface of another of the sections according to some embodiments of the invention.

This specification describes exemplary embodiments and applications of the invention. The invention, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," or "coupled to" are used herein, one element (e.g., a material, a layer, a substrate, etc.) can be "on," "attached to," or "coupled to" another element regardless of whether the one element is directly on, attached to, or coupled to the other element or there are one or more intervening elements between the one element and the other element. Also, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent. The term "ones" means more than one.

As used herein, the term "micro-object" can encompass one or more of the following: inanimate micro-objects such as microparticles, microbeads (e.g., polystyrene beads, Luminex™ beads, or the like), magnetic or paramagnetic beads (e.g. solid phase reversible immobilization (SPRI) beads), microrods, microwires, quantum dots, and the like; biological micro-objects such as cells (e.g., embryos, oocytes, sperms, cells dissociated from a tissue, blood cells, hybridomas, cultured cells, cells from a cell line, cancer cells, infected cells, transfected and/or transformed cells, reporter cells, and the like), liposomes (e.g., synthetic or derived from membrane preparations), lipid nanorafts, and the like; or a combination of inanimate micro-objects and biological micro-objects (e.g., microbeads attached to cells, liposome-coated micro-beads, liposome-coated magnetic beads, or the like). Lipid nanorafts have been described, e.g., in Ritchie et al. (2009) "Reconstitution of Membrane Proteins in Phospholipid Bilayer Nanodiscs," Methods Enzymol., 464:211-231.

As used herein, the term "cell" refers to a biological cell, which can be a plant cell, an animal cell (e.g., a mammalian cell), a bacterial cell, a fungal cell, or the like. A mammalian cell can be, for example, from a human, a mouse, a rat, a horse, a goat, a sheep, a cow, a primate, or the like, and can include any of the following cell types: oocytes, sperm, embryos, blood cells, immunological cells, macrophages, NK cells, T cells, B cells, hybridomas, cancer cells, stem cells, normal cells, infected cells (e.g., infected with a virus or other parasite), cells dissociated from a tissue, cultured cells, cells from a cell line, transfected and/or transformed cells, reporter cells, and the like.

A colony of biological cells is "clonal" if all of the living cells in the colony that are capable of reproducing are daughter cells derived from a single parent cell. The term "clonal cells" refers to cells of the same clonal colony.

The phrase "relatively high electrical conductivity" is used herein synonymously with the phrase "relatively low electrical impedance," and the foregoing phrases are interchangeable. Similarly, the phrase "relatively low electrical conductivity" is used synonymously with the phrase "relatively high electrical impedance," and the foregoing phrases are interchangeable.

A "fluidic circuit" means one or more fluidic structures (e.g., chambers, channels, holding pens, reservoirs, or the like), which can be interconnected. A "fluidic circuit frame" means one or more walls that define all or part of a fluidic circuit. A "holding pen" means a region in a microfluidic device, defined by walls of the fluidic circuit frame and having at least one opening to a different region of the microfluidic device (e.g., a channel, chamber, or another holding pen), which is configured to hold a volume of fluid and, optionally, one or more micro-objects. A holding pen can be an isolation chamber that contains an isolation region (e.g., an unswept region, as discussed below).

As used herein, the term "maintaining (a) cell(s)" refers to providing an environment comprising both fluidic and gaseous components and, optionally a surface, that provides the conditions necessary to keep the cells viable and/or expanding.

A "component" of a fluidic medium is any chemical or biochemical molecule present in the medium, including solvent molecules, ions, small molecules, antibiotics, nucleotides and nucleosides, nucleic acids, amino acids, peptides, proteins, sugars, carbohydrates, lipids, fatty acids, cholesterol, metabolites, or the like.

As used herein in reference to a fluidic medium, "diffuse" and "diffusion" refer to thermodynamic movement of a component of the fluidic medium down a concentration gradient.

The phrase "flow of a medium" means bulk movement of a fluidic medium primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase "substantially no flow" refers to a rate of flow of a fluidic medium that, averaged over time, is less than the rate of diffusion of components of a material (e.g., an analyte of interest) into or within the fluidic medium. The rate of diffusion of components of such a material can depend on, for example, temperature, the size of the components, and the strength of interactions between the components and the fluidic medium.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the device.

In some embodiments, a microfluidic device can comprise "swept" regions and "unswept" regions. A swept region is a region in which fluid is able to flow, whereas an unswept region is a region in which (given the configuration of the microfluidic device) fluid generally is unable to flow. An unswept region can be fluidically connected to a swept region, provided the fluidic connections are structured to enable diffusion but substantially no flow of media between the swept region and the unswept region. The microfluidic device can thus be structured to substantially isolate an unswept region from a flow of medium in a swept region, while enabling substantially only diffusive fluidic communication between the swept region and the unswept region. Microfluidic devices having swept and unswept regions have been described, for example, in U.S. patent application Ser. No. 14/520,568, filed Oct. 22, 2014, the entire contents of which are incorporated herein by reference.

A "microfluidic channel" or "flow channel" as used herein refers to flow region (or swept region) of a microfluidic device having a length that is significantly longer than both the horizontal and vertical dimensions. For example, the flow channel can be at least 5 times the length of either the horizontal or vertical dimension, e.g., at least 10 times the length, at least 25 times the length, at least 100 times the length, at least 200 times the length, at least 500 times the length, at least 1,000 times the length, at least 5,000 times the length, or longer. In some embodiments, the length of a flow channel is in the range of from about 100,000 microns to about 500,000 microns, including any range therebetween. In some embodiments, the horizontal dimension is in the range of from about 100 microns to about 300 microns (e.g., about 200 microns) and the vertical dimension is in the range of from about 25 microns to about 100 microns, e.g., from about 40 to about 50 microns. It is noted that a flow channel may have a variety of different spatial configurations in a microfluidic device, and thus is not restricted to a perfectly linear element. For example, a flow channel may be, or include one or more sections having, the following configurations: curve, bend, spiral, incline, decline, fork (e.g., multiple different flow paths), and any combination thereof. In addition, a flow channel may have different cross-sectional areas along its path, widening and constricting to provide a desired fluid flow therein.

The capability of biological micro-objects (e.g., biological cells) to produce specific biological materials (e.g., proteins, such as antibodies) can be assayed in a microfluidic device having a swept region, such as a channel, and an unswept region, such as an isolation pen (or isolation chamber). For example, sample material comprising biological micro-objects (e.g., cells) to be assayed for production of an analyte of interest can be loaded into a swept region of the microfluidic device. Ones of the biological micro-objects (e.g., mammalian cells, such as human cells) can be selected for particular characteristics and disposed in unswept regions. The remaining sample material can then be flowed out of the swept region and an assay material flowed into the swept region. Because the selected biological micro-objects are in unswept regions, the selected biological micro-objects are not substantially affected by the flowing out of the remaining sample material or the flowing in of the assay material. The selected biological micro-objects can be allowed to produce the analyte of interest, which can diffuse from the unswept regions into the swept region, where the analyte of interest can react with the assay material to produce localized detectable reactions, each of which can be correlated to a particular unswept region. Any unswept region associated with a detected reaction can be analyzed to determine which, if any, of the biological micro-objects in the unswept region are sufficient producers of the analyte of interest.

Similarly, biological micro-objects, such as cells, can be cultured or grown, after being placed in an unswept region (e.g., isolation region of an isolation chamber), by flowing culture medium though a swept region (e.g., a flow channel) to which the unswept region is fluidically connected. As the biological micro-objects are being cultured, nutrients from the culture medium in the swept region will diffuse into the unswept region, where they can be absorbed and used by the biological micro-objects, while waste products produced by the biological micro-objects and released into the unswept region can diffuse out of the unswept region and into the swept region, at which point the waste products can be flowed away (e.g., out of the microfluidic device).

Figure 1B:
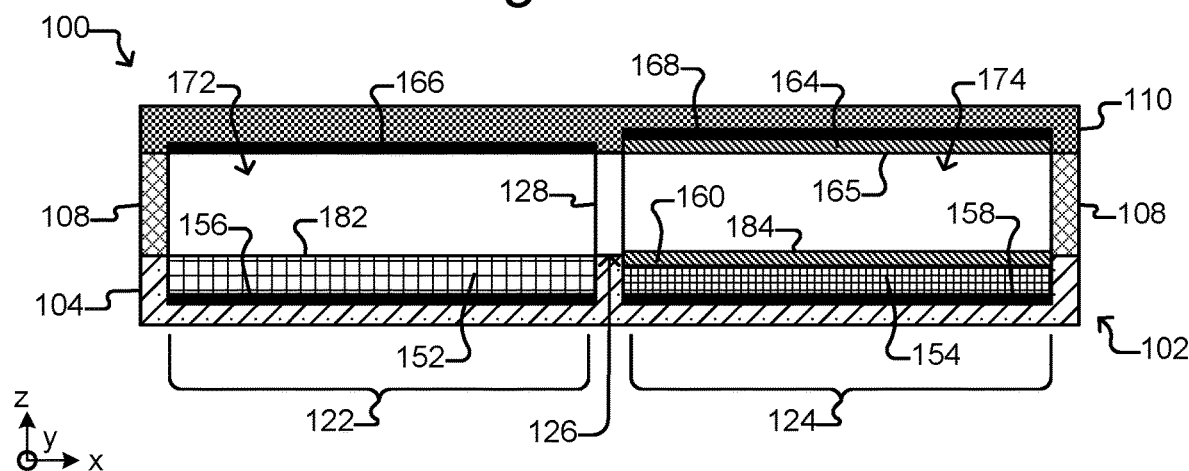
FIG. 1B is a cross-sectional side view of the microfluidic apparatus of FIG. 1A.
Figure 1C:
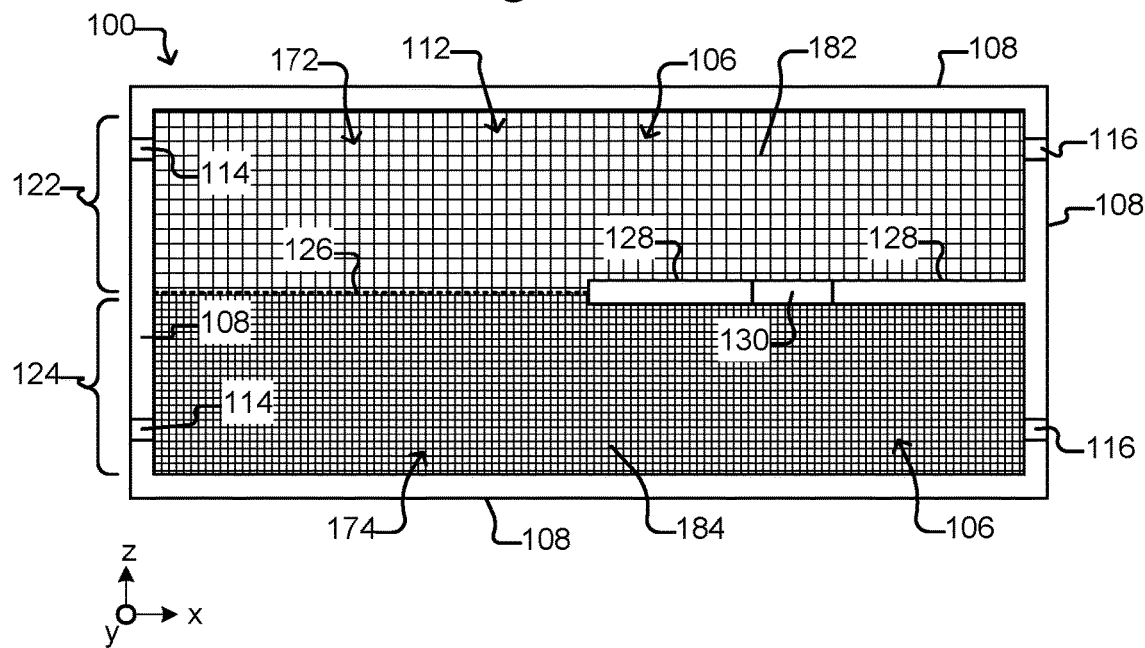
FIG. 1C is a top view of the microfluidic apparatus of FIG. 1A with the cover removed.

In some embodiments, a microfluidic apparatus can comprise a dielectrophoresis (DEP) configured section for holding a liquid medium and selectively inducing net DEP forces in the liquid medium. The microfluidic apparatus can also comprise an electrowetting (EW) configured section for holding another liquid medium in contact with an electrowetting surface and selectively changing an effective wetting property of the electrowetting surface. FIGS. 1A-1C illustrate an example of such a microfluidic apparatus 100. FIG. 1A also illustrates examples of control equipment 132 for controlling operation of the apparatus 100.

Figure 2:
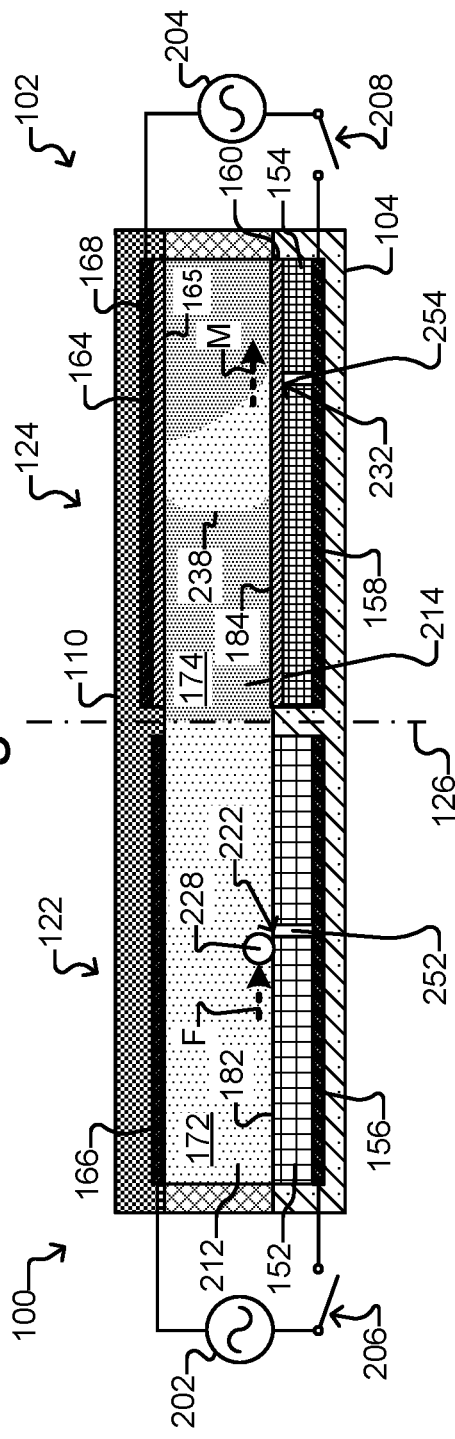
FIG. 2 is a cross-sectional side view of the micro-fluidic device of FIG. 1A with liquid media in its sections and connected to biasing devices according to some embodiments of the invention.

As shown, the apparatus 100 can comprise an enclosure 102, which can comprise a plurality (two are shown but there can be more) of sections 122, 124 each configured to hold a liquid medium (not shown in FIGS. 1A-1C, but depicted as 212, 214 in FIG. 2). The first section 122 can comprise a first surface 182 and be further configured to selectively generate net DEP forces on micro-objects (not shown) in a liquid medium in contact with the first surface 182. The first section 122 is thus referred to hereinafter as a DEP configured section or a DEP configuration 122 of the enclosure 102. The second section 124 can comprise an electrowetting surface 184 and can further be configured to selectively change an effective wetting property of the electrowetting surface 184. The second section 124 is thus referred to hereinafter as an electrowetting (EW) configured section or an EW configuration 124 of the enclosure 102.

Although the apparatus 100 can be physically structured in many different ways, in the example shown in FIGS. 1A-1C, the enclosure 102 is depicted as comprising a structure 104 (e.g., a base), a fluidic circuit frame 108, and a cover 110. As shown, the fluidic circuit frame 108 can be disposed on an inner surface 106 of the structure 104, and the cover 110 can be disposed over the fluidic circuit frame 108. With the structure 104 as the bottom and the cover as the top 110, the fluidic circuit frame 108 can define a fluidic circuit comprising, for example, interconnected fluidic chambers, channels, pens, reservoirs, and the like. Although the structure 104 is shown in FIGS. 1A and 1B as comprising the bottom of the apparatus 100 and the cover 110 is illustrated as the top, the structure 104 can be the top and the cover 110 can be the bottom of the apparatus 100.

In the example illustrated in FIGS. 1A-1C, the fluidic circuit frame 108 defines a chamber 112. A first section 172 of the chamber 112 corresponding to a DEP configured section 122 is hereinafter referred to as the first chamber section 172, and a second section of the chamber 112 corresponding to an EW section 124 of the enclosure 102 is hereinafter referred to as the second chamber section 174. As also shown, the chamber 112 can include one or more inlets 114 and one or more outlets 116.

In some embodiments, the enclosure 102 can comprise a physical barrier 128 between the first chamber section 172 and the second chamber section 174, and such a physical barrier 128 can comprise one or more passages 130 from the first chamber section 172 of the enclosure 102 to the second chamber section 174. In the example illustrated in FIGS. 1A-1C, such a physical barrier 128 is shown along only a portion of a boundary 126 between the first chamber section 172 and the second chamber section 174. Alternatively, the physical barrier 128 can extend the entirety of the boundary 126 or be located on a different portion of the boundary 126. Regardless, the physical barrier 128 can be part of the fluidic circuit frame 108 (as shown), or the physical barrier 128 can be structurally distinct from the fluidic circuit frame 108. Although one physical barrier 128 is shown, there can be more than one such physical barrier 128 disposed on the boundary 126.

The structure 104 can comprise, for example, a substrate (e.g., a photoconductive substrate or a circuit substrate) or a plurality of such substrates that are interconnected. The fluidic circuit frame 108 can comprise a material, which can be flexible or gas permeable. Alternatively, the material need not be flexible and/or gas permeable. Suitable examples of materials that the circuit frame 108 can comprise include rubber, plastic, an elastomer, silicone, photo-patternable silicon (PPS), polydimethylsiloxane ("PDMS"), or the like. The cover 110 can be an integral part of the fluidic circuit frame 108, or the cover 110 can be a structurally distinct element (as illustrated in FIGS. 1A-1C). The cover 110 can comprise the same materials as the fluidic circuit frame 108. Thus, the cover 110 can be made from or comprise a flexible material, as discussed above. Alternatively, the cover 110 can be made from or comprise a rigid material (e.g., glass, including ITO-coated glass). Regardless, the cover 110 and/or the structure 104 can be transparent to light.

As shown in FIG. 1B, in some embodiments, the DEP configuration 122 of the enclosure 102 can comprise a biasing electrode 156, a DEP section 152 of the structure 104, and the first surface 182, all of which can be part of the structure 104. The DEP configuration 122 can also include a biasing electrode 166, which can be part of the cover 110. The foregoing can be located with respect to each other as illustrated in FIG. 1B. The first surface 182 can be an outer surface of the DEP section 152 or an outer surface of one or more materials (e.g., one or more coatings) (not shown) disposed on the DEP section 152. Examples of such coatings (not shown) on the first surface 182 include electrically insulating materials.

Similarly, the EW configuration 124 of the enclosure 102 can comprise a biasing electrode 158, an EW section 154 of the structure 104, a dielectric layer 160, and the electrowetting surface 184, all of which can be part of the structure 104. The EW configuration 124 can also include a hydrophobic surface 165, a layer 164 (e.g., a dielectric material), and a biasing electrode 168, all of which can be part of the cover 110. The foregoing can be located with respect to each other as shown in FIG. 1B. The dielectric layer 160 and/or the layer 164 can comprise a hydrophilic material such as silicon oxide ($SiO_2$), aluminum oxide ($Al_3O_2$), or the like. Alternatively, the dielectric layer 160 and/or the layer 164 can comprise a hydrophobic material such as a hydrophobic polymer (e.g., a perfluoro-polymer, such as CYTOP, or a poly(p-xylylen)polymer, such as parylene). The electrowetting surface 184, which can be hydrophobic, can be an outer surface of the dielectric layer 160 or an outer surface of one or more materials (not shown) disposed on the dielectric layer 160. Similarly, the hydrophobic surface 165 can be an outer surface of the layer 164 or an outer surface of one or more materials (not shown) disposed on the layer 164. An example of a material that can be disposed on the dielectric layer 160 and/or the layer 164 includes polytetrafluoroethylene (PTFE, a.k.a. Teflon™ by Dupont™).

As shown in FIG. 1A, an electrical biasing device 118 can be connected to the apparatus 100. The electrical biasing device 118 can, for example, comprise one or more voltage or current sources. As also shown in FIG. 1A, examples of the control equipment include a master controller 134, a DEP module 142 for controlling the DEP configuration 122 of the enclosure 102, and an EW module 144 for controlling the EW configuration 124 of the enclosure 102. The control equipment 132 can also include other modules 140 for controlling, monitoring, or performing other functions with respect to the apparatus 100.

The master controller 134 can comprise a control module 136 and a digital memory 138. The control module 136 can comprise, for example, a digital processor configured to operate in accordance with machine executable instructions (e.g., software, firmware, microcode, or the like) stored in the memory 138. Alternatively or in addition, the control module 136 can comprise hardwired digital circuitry and/or analog circuitry. The DEP module 142, EW module 144, and/or the other modules 140 can be similarly configured. Thus, functions, processes, acts, actions, or steps of a process discussed herein as being performed with respect to the apparatus 100 or any other microfluidic apparatus can be performed by one or more of the master controller 134, DEP module 142, EW module 144, or other modules 140 configured as discussed above.

FIG. 2 illustrates an example configuration of the apparatus 100. As shown, a first liquid medium 212 can be disposed on the first surface 182 in the first chamber section 172, and a second liquid medium 214 can be disposed on the electrowetting surface 184 in the second chamber section 174. The first liquid medium 212 and the second liquid medium 214 can be different mediums. For example, the second liquid medium 214 can be immiscible with respect to the first liquid medium 212. The first liquid medium 212 can be, for example, an aqueous medium, such as water, an aqueous buffer (e.g., a phosphate buffer, a tris(hydroxymethyl)amionmethane (Tris) buffer, or the like), an aqueous solution (e.g., containing one or more soluble active agents), cell culture medium, etc. The second liquid medium 214 can be immiscible in an aqueous medium. Examples of the second liquid medium 214 can include oil based media. Examples of suitable oils include gas permeable oils such as fluorinated oils. Fluorocarbon based oils are also examples of suitable oils.

As also shown in FIG. 2, a first biasing device 202 can be connected to the biasing electrodes 156, 166 of the DEP configuration 122 of the enclosure 102, and a second biasing device 204 can be connected to the biasing electrodes 158, 168 of the EW configuration 124 of the enclosure 102. The first biasing device 202 can be, for example, an alternating current (AC) voltage or current source, and the second biasing device 204 can similarly be an AC voltage or current source. A switch 206 can selectively connect the first biasing device 202 to and disconnect the first biasing device 202 from the DEP configuration 122. Another switch 208 can similarly connect the second biasing device 204 to and disconnect the second biasing device 204 from the EW configuration 124. The biasing devices 202, 204 and switches 206, 208 can be part of the biasing device 118 of FIG. 1A.

The DEP section 152 of the structure 104 can be configured to have a relatively high electrical impedance (i.e., a relatively low electrical conductivity) between the first medium 212 and the biasing electrode 156 except when a DEP electrode 222 at the first surface 182 is activated. (The DEP section 152 can be an example of an electrode activation substrate.) Activating the DEP electrode 222 can create a relatively low electrical impedance (i.e., a relatively high electrical conductivity) path 252 from the DEP electrode 222 to the biasing electrode 156. While the DEP electrode 222 is deactivated, the majority of the voltage drop due to the first biasing device 202 from the DEP biasing electrode 166 to the DEP biasing electrode 156 can be across the DEP section 152. While the DEP electrode 222 is activated and creating the relatively low electrical impedance path 252, however, the majority of the voltage drop in the vicinity of the path 252 can be across the first medium 222, which can create a net DEP force (F) in the first medium 212 in the vicinity of the activated DEP electrode 222. Depending on such characteristics as the frequency of the biasing device 202 and the dielectric properties of the first medium 212 and/or micro-objects 228 in the medium 212, the DEP force F can attract or repel a nearby micro-object 228 in the first medium 212. Many DEP electrodes like DEP electrode 222 can be selectively activated and deactivated over some, most, or the entirety of the first surface 182. By selectively activating and deactivating such DEP electrodes (like 222), one or more micro-objects 228 in the first medium 212 of the DEP section 152 of the enclosure 102 can be selected (e.g., captured) and moved (e.g., in a directed manner) in the medium 212. Equipment 132 (see FIG. 1A) can control activation and deactivation of such DEP electrodes (e.g., 222). As will be seen, DEP electrodes (like 222) can be fixed in a particular location, in the manner of conventional electrodes (e.g., metal electrodes), phototransistors, or photo-actuated electrodes. Alternatively, DEP electrodes (like 222) can be virtual electrodes that are located at positions where electromagnetic radiation is incident on a photoconductive material, as occurs when light of an appropriate frequency is incident on a layer of amorphous silicon that is connected to a biasing electrode (like 156).

The EW section 154 of the structure 104 can similarly be configured to have a relatively high electrical impedance (i.e., relatively low electrical conductivity) except when an EW electrode 232 at the electrowetting surface 184 is activated. (The EW section 154 can also be an example of an electrode activation substrate.) Activating such an EW electrode 232 can create a relatively low electrical impedance (i.e., a relatively high electrical conductivity) path 254 from the EW electrode 232 to the EW biasing electrode 158. While the EW electrode 232 is deactivated (and the EW section 154 has a relatively high electrical impedance), the voltage drop due to the second biasing device 204 from the EW biasing electrode 168 to the EW biasing electrode 158 can be greater across the EW section 154 than across the dielectric layer 160. While the EW electrode 232 is activated and creating the relatively low electrical impedance path 254, however, the voltage drop across the EW section 154 can become less than the voltage drop across the dielectric layer 160.

The foregoing can change a force across the EW surface 184, which can change an effective wetting property of the EW surface 184 in the vicinity of the activated EW electrode 232. For example, as noted, the EW surface 184 can be hydrophobic. Activating an EW electrode 232 can increase a Coulombic force across the EW surface 184 (due to increased charge density at the surface of the dielectric layer 160) in the vicinity of the activated EW electrode 232. The increased Coulombic force can be sufficient to overcome the cohesive forces between molecules of a nearby droplet, effectively reducing the hydrophobicity of the EW surface 184 in the vicinity of the activated EW electrode 232. The foregoing can move the droplet on the EW surface 184.

Many EW electrodes (like 232) can be selectively activated and deactivated over some, most, or the entirety of the electrowetting surface 184. By selectively activating and deactivating such EW electrodes (like 232), droplets of liquid medium 214 or another liquid (not shown) in the second liquid medium 214 can be moved along the electrowetting surface 184. Equipment 132 (see FIG. 1A) can control activation and deactivation of such EW electrodes (e.g., 232). As will be seen, such EW electrodes (like 232) can be fixed in a particular location, in the manner of conventional electrodes (e.g., metal electrodes), phototransistors, or photo-actuated electrodes. Alternatively, EW electrodes (like 232) can be virtual electrodes that are located at positions where electromagnetic radiation is incident on a photoconductive material, as occurs when light of an appropriate frequency is incident on a layer of amorphous silicon that is connected to a biasing electrode (like 158).

FIGS. 3-7 illustrate examples of the DEP configuration 122 and the EW configuration 124 of the enclosure 102.

Figure 3:
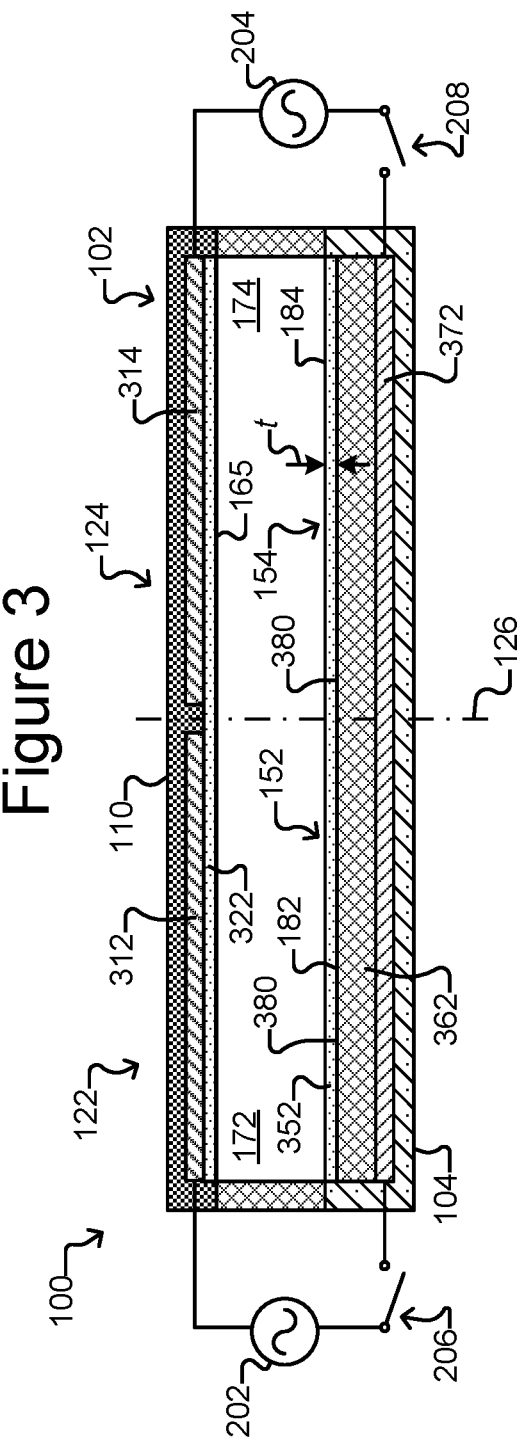
FIG. 3 illustrates an example of a DEP configuration and a controllable electrowetting (EW) configuration of the enclosure of the device of FIG. 1A according to some embodiments of the invention.

In the examples shown in FIG. 3, the structure 104 of the enclosure 102 can comprise a layer 352 of dielectric material, an electrode activation substrate 362, and a biasing electrode 372. The first surface 182 can be a surface of the electrode activation substrate 362, and the electrowetting surface 184 can be an outer surface of the dielectric layer 352, which can be hydrophobic. As also shown, the cover 110 can comprise a DEP biasing electrode 312 and an EW biasing electrode 314. The cover 110 can also include a layer 322 of electrically insulating material, which can extend across the DEP section 122 and the EW section 124 as illustrated. Alternatively, layer 322 can be disposed in the EW section 124 without extending into the DEP section 122, and of course, the layer 322 need not be present in some embodiments. The hydrophobic surface 165 can be an outer surface of the layer 322, which can be hydrophobic. The DEP biasing device 202 can be connected to the DEP biasing electrode 312 and the biasing electrode 372, and the EW biasing device 204 can be connected to the EW biasing electrode 314 and the biasing electrode 372.

Generally as shown in FIG. 3, each of the dielectric layer 352, the electrode activation substrate 362, and the biasing electrode 372 can be a continuous layer or substrate that extends across both the DEP section 172 and the EW section 174 of the chamber 112. For example, each of the dielectric layer 352, the electrode activation substrate 362, and the biasing electrode 372 can be a continuous layer or substrate that extends across substantially the entirety of the structure 104. As also shown, the electrically insulating layer 322 of the cover 110 can also be a continuous layer that extends through both the DEP section 172 and the EW section 174 of the chamber 112. FIG. 3 depicts the DEP biasing electrode 312 and the EW biasing electrode 314 of the cover 110 as two different unconnected electrodes each corresponding to one but not the other of the DEP section 172 or the EW section 174. The DEP biasing electrode 312 and the EW biasing electrode 314 can alternatively be a continuous biasing electrode like the biasing electrode 372. Similarly, any of the insulating layer 322, the dielectric layer 352, the electrode activation substrate 362, and/or the biasing electrode 372 can be two distinct structures each corresponding to one but not the other of the DEP section 172 or the EW section 174, as the DEP biasing electrode 312 and EW biasing electrode 314 are depicted in FIG. 3. For example, the insulating layer 322 can be disposed only on the biasing electrode 314 in the EW section 124 but not on the biasing electrode 312 in the DEP section 122. The insulating layer 322 can comprise a hydrophobic material, or alternatively, a hydrophilic material examples of which can be as discussed above. Examples of the dielectric material 352 can also be as discussed above.

In the example shown in FIG. 3, the DEP biasing electrode 312 is an example of the biasing electrode 166 in FIG. 2. Similarly, the portion of the biasing electrode 372 to the left of the boundary 126 in FIG. 3 is an example of the biasing electrode 156 in FIG. 2, and the portion of the electrode activation substrate 362 to the left of the boundary 126 is an example of the DEP section 152 in FIG. 2. Likewise, the EW biasing electrode 314 in FIG. 3 is an example of the biasing electrode 168 in FIG. 2; the portion of the electrode activation substrate 362 to the right of the boundary 126 in FIG. 3 is an example of the EW section 154 in FIG. 2; the portion of the dielectric layer 352 in FIG. 3 to the right of the boundary 126 is an example of dielectric layer 160 in FIG. 2; and the portion of the insulating layer 322 in FIG. 3 to the right of the boundary 126 is an example of the layer 164 in FIG. 2.

In the example shown in FIG. 2, the EW section 154 but not the DEP section 152 of the structure 104 is illustrated as comprising a dielectric layer 160, yet the example shown in FIG. 3 shows the dielectric layer 352 extending across both the DEP configuration 122 and the EW configuration 124 of the enclosure 102. In some embodiments, the thickness t of the dielectric layer 352 can be sufficiently thin that a DEP electrode like 222 (see FIG. 2) activated at an outer surface 380 of the electrode activation substrate 362 (e.g., at the region 412 in FIG. 4 or the region 512 in FIG. 5) can effectively form an electrical connection through the dielectric layer 352 with the first medium 212 in the first chamber section 172 of the enclosure 104. Alternatively, or in addition, the DEP biasing device 202 can be operated such that the capacitive effect of the portion of the dielectric layer 352 to the left of the boundary 126 in FIG. 3 is effectively shorted, and the EW biasing device 204 can be operated such that the capacitive effect of the portion of the dielectric layer 352 to the right of the boundary 126 is not shorted.

For example, the portion of the dielectric layer 352 to the left of the boundary 126 in FIG. 3 can form a first effective capacitor (not shown) between the liquid medium 212 in the first chamber section 172 and any relatively high electrical conductivity region (e.g., like a DEP electrode 222 in FIG. 2) formed at the outer surface 380 of the electrode activation substrate 362. Similarly, the portion of the dielectric layer 352 to the right of the boundary 126 in FIG. 3 can form a second effective capacitor (not shown) between the liquid medium 214 in the second chamber section 174 and any relatively high electrical conductivity region (e.g., like an EW electrode 232) formed at the outer surface 380 of the electrode activation substrate 362. The DEP biasing device 202 can be operated at a frequency $f_i$ that is sufficiently high to effectively short the first effective capacitor (not shown) and thus effectively eliminate the capacitive effect of the portion of the dielectric layer 352 to the left of the boundary 126 in FIG. 3. The EW biasing device 204, however, can be operated at a lower frequency $f_2$, which can be a frequency at which the capacitive effect of the second effective capacitor (not shown) is significant.

The apparatus 100 can be operated in a DEP mode in which, for example, the switch 206 is closed, thereby connecting the DEP biasing device 202 to the biasing electrodes 312, 372, but the switch 208 is open, thereby disconnecting the EW biasing device 204 from the biasing electrodes 314, 372. The apparatus 100 can similarly be operated in an EW mode in which the switch 206 is open but the switch 208 is closed. The equipment 132 (see FIG. 1A) can control the switches 206, 208.

Figure 4:
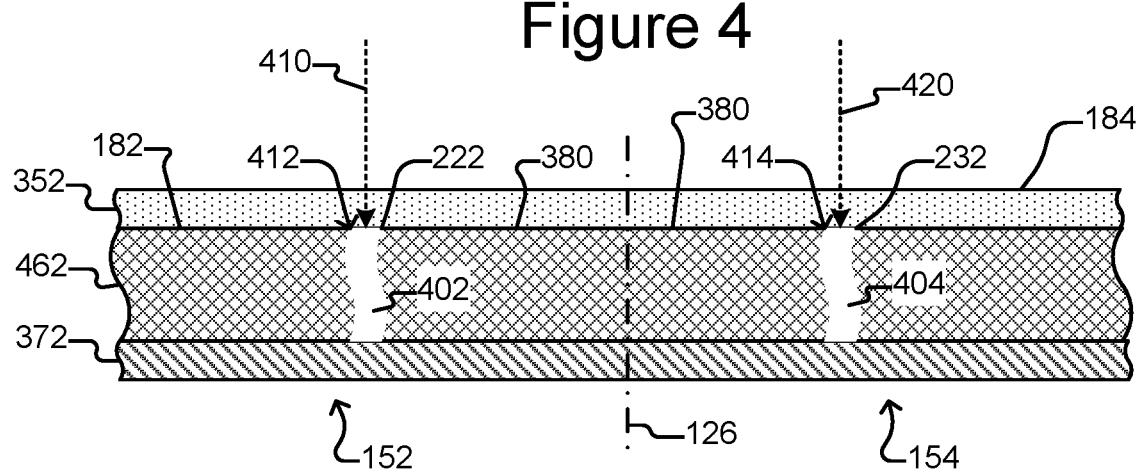
FIG. 4 is an example of the electrode activation substrate of FIG. 3 configured as photoconductive material according to some embodiments of the invention.
Figure 5:
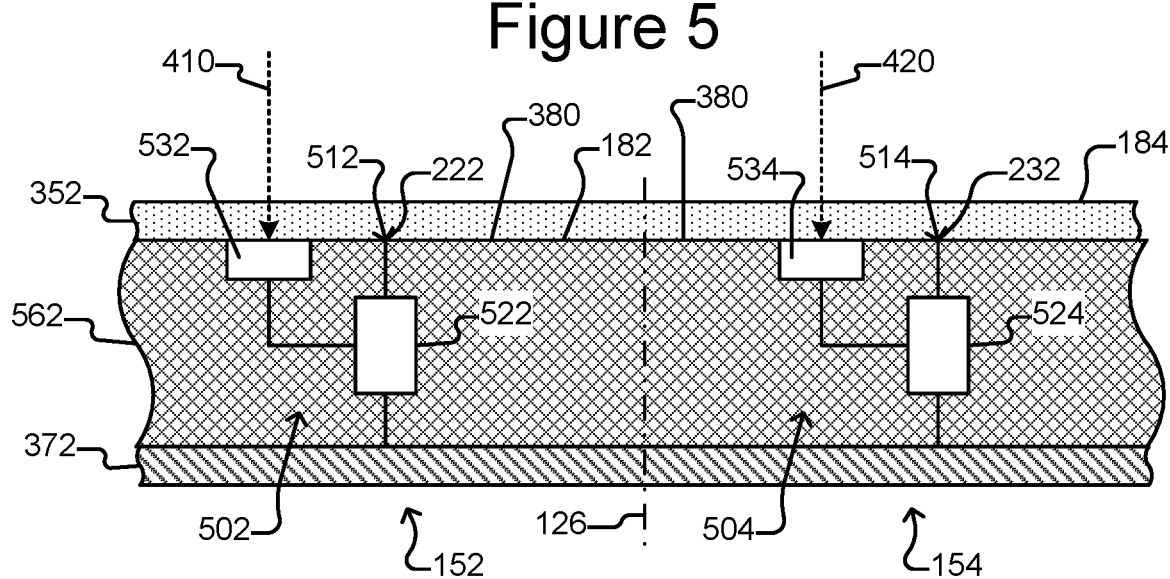
FIG. 5 is another example of the electrode activation substrate of FIG. 3 configured as a circuit substrate according to some embodiments of the invention.

The electrode activation substrate 362 can be configured such that the DEP electrodes (like 222) and the EW electrodes (like 232) (see FIG. 2) are virtual electrodes and/or fixed electrodes. FIG. 4 illustrates an example in which the electrode activation substrate 362 comprises photoconductive material 462, and the DEP electrode 222 and the EW electrode 232 are virtual electrodes. FIG. 5 shows an example in which the electrode activation substrate 362 comprises a circuit substrate 562, and the DEP electrode 222 and the EW electrode 232 are fixed.

As noted, in the example shown in FIG. 4, the electrode activation substrate 362 can comprise photoconductive material 462, which can be a material that has a relatively high electrical impedance except when exposed directly to light. Examples of photoconductive material include semiconductor materials such as amorphous silicon. As shown, when light 410 is directed onto a relatively small region 412 of the photoconductive material 462 of the DEP section 152 of the structure 104, a relatively high electrically conductive path 402 is formed at the region 412 through the photoconductive material 462 to the biasing electrode 372. The conductive path 402 corresponds to the path 252 in FIG. 2, and the light 410 thus activates a virtual DEP electrode 222 at the region 412.

As also shown in FIG. 4, light 420 directed onto a relatively small region 414 of the EW section 154 of the structure 104 can similarly create a relatively high electrically conductive path 404 at the region 414 through the photoconductive material 462 to the biasing electrode 372. The conductive path 404 corresponds to the path 254 in FIG. 2, and the light 420 thus activates a virtual EW electrode 232 at the region 412.

In the embodiment shown in FIG. 4, DEP electrodes (like 222) can be activated in any desired pattern anywhere on the photoconductive material 462 by directing light 410 in the desired pattern onto the photoconductive material 462. Such DEP electrodes 222 can be deactivated by removing the light 410. EW electrodes (like 232) can similarly be activated and deactivated in any desired pattern anywhere on the photoconductive material 462 in accordance with a pattern of the light 414. The DEP electrodes (like 222) and the EW electrodes (like 232) are thus virtual electrodes. The DEP module 142 of FIG. 1A can comprise a light source (not shown), and the DEP module 142 and/or the master controller 134 can control the light source to direct changing patterns of light into the apparatus 100 to selectively activate and deactivate such DEP electrodes (like 222) and EW electrodes (like 232) anywhere on the photoconductive material 462.

In the example shown in FIG. 5, the electrode activation substrate 362 can comprise a circuit substrate 562, which can comprise a base material that has a relatively high electrical impedance but includes circuits for making relatively high electrical conductivity connections through the substrate. For example, a DEP electrode circuit 502 in the DEP section 152 of the structure 104 can comprise a switch 522 that provides a relatively high electrical conductivity connection (corresponding to the path 252 in FIG. 2) from a relatively small fixed region 512 through the substrate 562 to the biasing electrode 372. The switch 522 can be selectively opened and closed to thereby selectively create a relatively high electrical impedance path from the region 512 to the biasing electrode 372 or a relatively high electrical conductivity path. In the example shown in FIG. 5, the switch 522 is controlled by a photo element 532, which can open and close the switch 522 in response to a directed light beam 410. Alternatively, the switch 522 can be controlled by an external control module (e.g., the DEP module 142 of FIG. 1A) via a control input (not shown). DEP electrode circuits like circuit 502 can be provided throughout the DEP section 152 of the structure 104, and a pattern of fixed DEP electrodes (like 222) can thus be provided through the DEP section 152. Such fixed DEP electrodes 222 can be activated and deactivated with light 410 or through external (e.g., electrical) control.

The DEP module 142 of FIG. 1A can comprise a light source (not shown), and the DEP module 142 and/or the master controller 134 can control the light source to direct changing patterns of light 410 into the apparatus 100 to selectively activate and deactivate photo-actuated DEP electrodes (like 222 in FIGS. 4 and 5). Alternatively, if some or all of the DEP electrodes are hardwired, the DEP module 142 and/or the master controller 134 can selectively control activation and deactivation of such DEP electrodes (like 222) in changing patterns.

The EW section 154 of the structure 104 can include similar EW electrode circuits 504. For example, an EW electrode circuit 504 in the EW section 154 of the structure 104 can comprise a switch 524 that provides a high conductivity electrical connection (corresponding to the path 254 in FIG. 2) from a relatively small fixed region 514 through the substrate 562 to the biasing electrode 372. The switch 524 can be selectively opened and closed to thereby selectively create a relatively high electrical impedance path from the region 514 to the biasing electrode 372 or a relatively high electrical conductivity path. In the example shown in FIG. 5, the switch 524 is controlled by a photo element 524, which can open and close the switch 524 in response to a directed light beam 420. Alternatively, the switch 524 can be controlled by an external control module (e.g., the EW module 144 of FIG. 1A) by an electrical control input (not shown). EW electrode circuits like circuit 504 can be provided throughout the EW section 154 of the structure 104, and a pattern of fixed EW electrodes (like 232) can thus be provided throughout the EW section 154. Such EW electrodes can be activated and deactivated with light 412 or through external control.

The EW module 144 of FIG. 1A can comprise a light source (not shown), and the EW module 144 and/or the master controller 134 can control the light source to direct changing patterns of light 420 into the apparatus 100 to selectively activate and deactivate photo-actuated EW electrodes (like 232 in FIGS. 4 and 5). Alternatively, if some or all of the DEP electrodes are hardwired, the EW module 144 and/or the master controller 134 can selectively control activation and deactivation of such EW electrodes (like 232) in changing patterns.

In some embodiments, switch 522 and/or switch 524 in FIG. 5 can comprise a transistor. For example, switch 522 and/or switch 524 can comprise a transistor that can be activated and deactivated by photo element 532 and/or 534. Alternatively, switch 522 and/or 534 configured as a transistor can be activated and deactivated by a hardwired control connection (not shown). As yet another example, switch 522 and/or switch 524 can comprise a photo transistor activated by directing light 410 or 420 onto the photo transistor itself and deactivated by removing the light 410 or 420 from the phototransistor. If the switch 522 and/or 524 is configured as a hardwired transistor or a photo transistor, there may be no need for photo element 532 or 534. In some embodiments, the DEP electrode 222 in FIG. 5 can comprise a fixed physical electrode at region 512 to which the switch 522 is electrically connected. The EW electrode 232 can similarly comprise a fixed physical electrode at region 514 to which the switch 524 is electrically connected.

Figure 6:
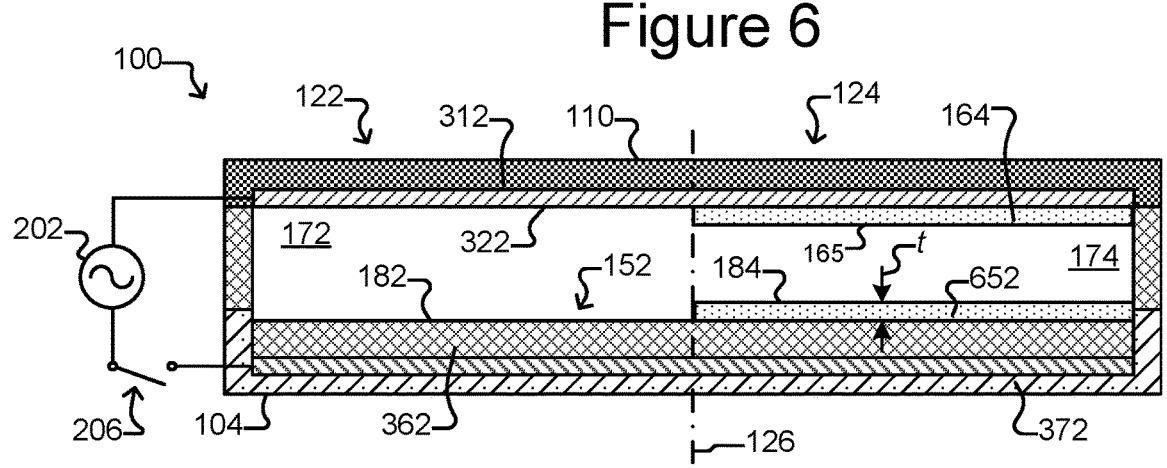
FIG. 6 illustrates another example of a DEP configuration and an EW configuration of the enclosure of the device of FIG. 1A according to some embodiments of the invention.
Figure 7:
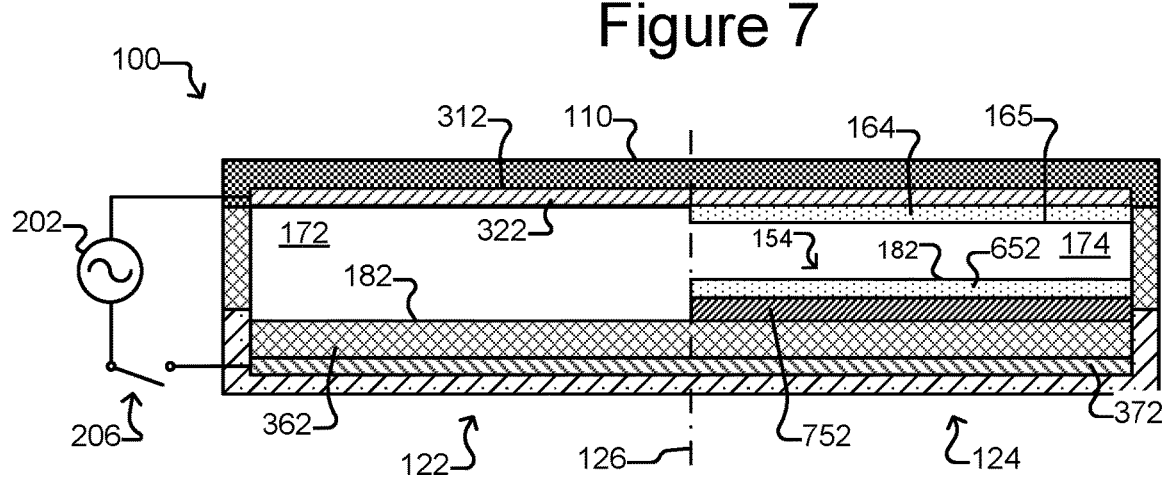
FIG. 7 is yet another example of a DEP configuration and an EW configuration of the enclosure of the device of FIG. 1A according to some embodiments of the invention.

As noted, FIGS. 6 and 7, like FIG. 3, illustrate example configurations of the DEP configuration 122 and EW configuration 124 of the enclosure 102.

The configuration illustrated in FIG. 6 is similar to FIG. 3 except that a dielectric layer 652 replaces the dielectric layer 352. The dielectric layer 652 forms the electrowetting surface 184 of the second chamber section 174 but not the first surface 182 of the first chamber section 172. Thus, the dielectric layer 652 is part of the EW configuration 124 of the enclosure 104 but not the DEP configuration 122. Because the dielectric layer 652 does not extend across the first surface 182 of the DEP configuration 122, the thickness t of the dielectric layer 652 can be greater than the thickness t of the dielectric layer 352 in FIG. 3. Otherwise, the dielectric layer 652 can be like and can comprise the same materials as the dielectric layer 352.

The configuration of FIG. 7 is similar to FIG. 6 except the configuration of FIG. 7 includes an additional dielectric layer 752 between the dielectric layer 652 and the electrode activation substrate 362. The dielectric layer 652 and the dielectric layer 752 can be part of the EW configuration 124 of the enclosure 104, but those layers are not part of the DEP configuration 122. The dielectric layer 752 can be like and can comprise the same materials as any dielectric layer (e.g., 352) mentioned herein.

Although not shown in FIG. 7, a biasing electrode can be located in the EW section 124 between the additional dielectric layer 752 and the portion of the electrode activation substrate 362 that is in the EW section 124. The biasing device 204 (see FIG. 2) can be connected to the portion of the biasing electrode 312 (which can be bifurcated and thus comprise a portion in the DEP section 122 and a separate electrically isolated portion in the EW section 124) that is to the right of the boundary 126 in FIG. 7 and the biasing electrode (not shown) between the additional dielectric layer 752 and the portion of the electrode activation substrate 362 in the EW section 124 rather than to the biasing electrode 372.

Figure 8:
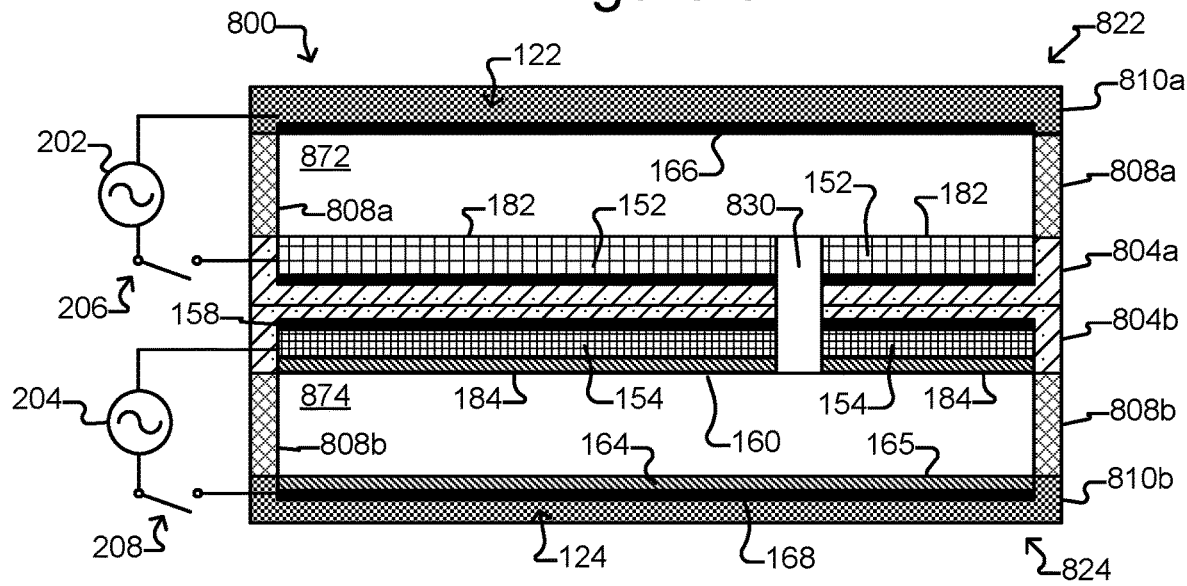
FIG. 8 is a cross-sectional side view of a microfluidic apparatus with multiple stacked sections according to some embodiments of the invention.

FIGS. 1A-1C show the first chamber section 172 and the second section 174 of the enclosure 104 side-by-side (e.g., substantially in a same plane). The foregoing, however, is merely an example, and other configurations are possible. FIG. 8 illustrates an example in which such sections are stacked.

FIG. 8 illustrates a microfluidic apparatus 800 that can comprise a first sub-enclosure 822 stacked on a second sub-enclosure 824. For example, each sub-enclosure 822, 824 can comprise a structure 804, a fluidic circuit frame 808, and a cover 810 each of which can be the same as or similar to the structure 104, fluidic circuit frame 108, and cover 110 of FIGS. 1A-1C. Although two stacked sub-enclosures 822, 824 are shown in FIG. 8, there can be more such stacked sub-enclosures.

Either or all of the sub-enclosures 822, 824 can be configured as a DEP configured device and/or an EW configured device. That is, although the first sub-enclosure 822 is illustrated as comprising a DEP configuration 122 and the second sub-enclosure 824 is shown as comprising an EW configuration 124, both sub-enclosures 822, 824 can comprise a DEP configuration (e.g., like 122) or an EW configuration (e.g., like 124). As yet another alternative, one or both of the sub-enclosures 822, 824 can be configured in part as a DEP configuration and in part as an EW configuration (e.g., one or both of the sub-enclosures 822, 824 can be configured like the apparatus 100 shown in FIGS. 1A-2).

As illustrated in FIG. 8, the first enclosure 822 can comprise a DEP configuration 122, and the second enclosure 824 can comprise an EW configuration 124 as discussed above. For example, the structure 804a of the first enclosure 822 can comprise the DEP section 152, including a first surface 182, and the cover 810a can comprise the biasing electrode 166, as discussed above. Similarly, the structure 804b of the second enclosure 822 can comprise the EW section 154, the dielectric layer 160, and the electrowetting surface 184, and the cover 810b can comprise the hydrophobic surface 165, the layer 164, and the biasing electrode 168, as discussed above.

The first sub-enclosure 822 can define a first section 872 for holding a liquid medium (e.g., the first liquid medium 212 shown in FIG. 2), and the DEP configuration 122 can select and manipulate micro-objects (e.g., like 228 in FIG. 2) in such a liquid medium in the first section 872. The second sub-enclosure 824 can similarly define a second section 874 for holding a liquid medium (e.g., the second liquid medium 214 shown in FIG. 2), and the EW configuration 124 can manipulate a liquid medium on the electrowetting surface 184, as discussed above, in the second section 874. As also shown, there can be one or more passages 830 (one is shown but there can be more) from the first section 872 to the second section 874. The sidewalls of such a passage 830 can be hydrophilic in which case an aqueous medium in the first section 872 can naturally enter and fill the passage 830. Alternatively, the sidewalls of the passage 830 can be hydrophobic.

Figure 9:
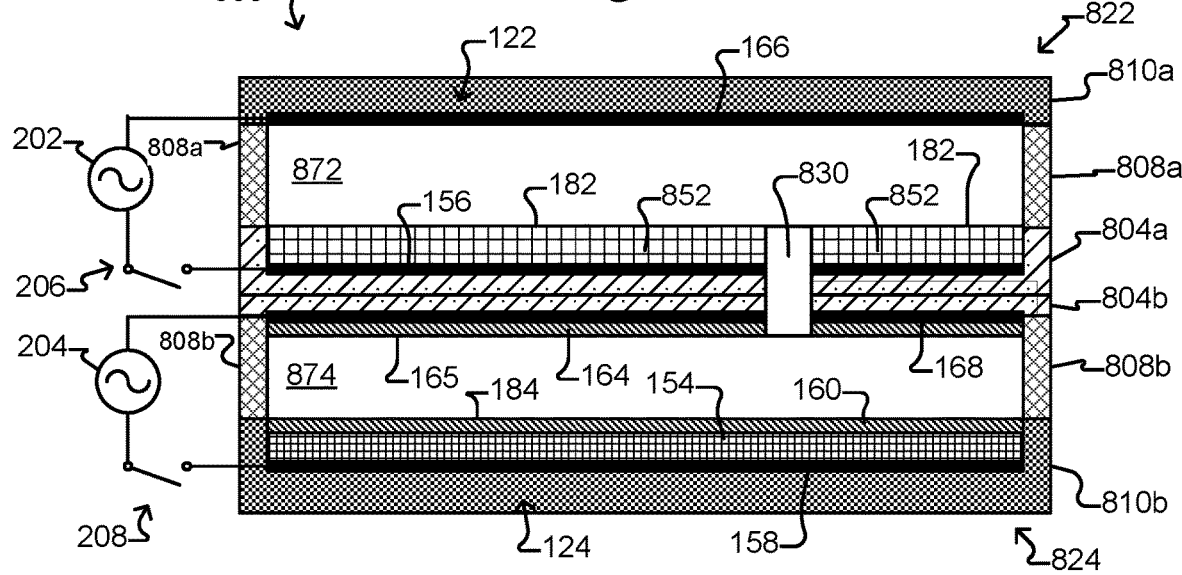
FIG. 9 illustrates another example of an embodiment of a microfluidic apparatus with multiple stacked sections according to some embodiments of the invention.

FIG. 9 illustrates another example of a microfluidic apparatus 900 that can be generally similar to the device 800 except that the positions of the biasing electrode 168, layer 164, and hydrophobic surface 165, on one hand, and the electrowetting surface 184, dielectric layer 160, EW section 154, and biasing electrode 158 are different (e.g., opposite) than the positions shown in FIG. 8.

Figure 10B:
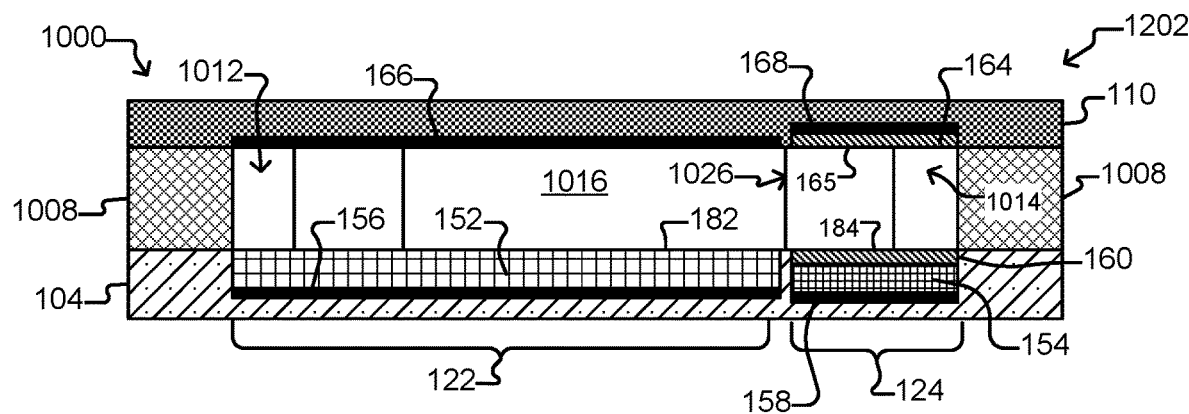
FIG. 10B is a side cross-sectional view of the microfluidic apparatus of FIG. 10A.
Figure 10C:
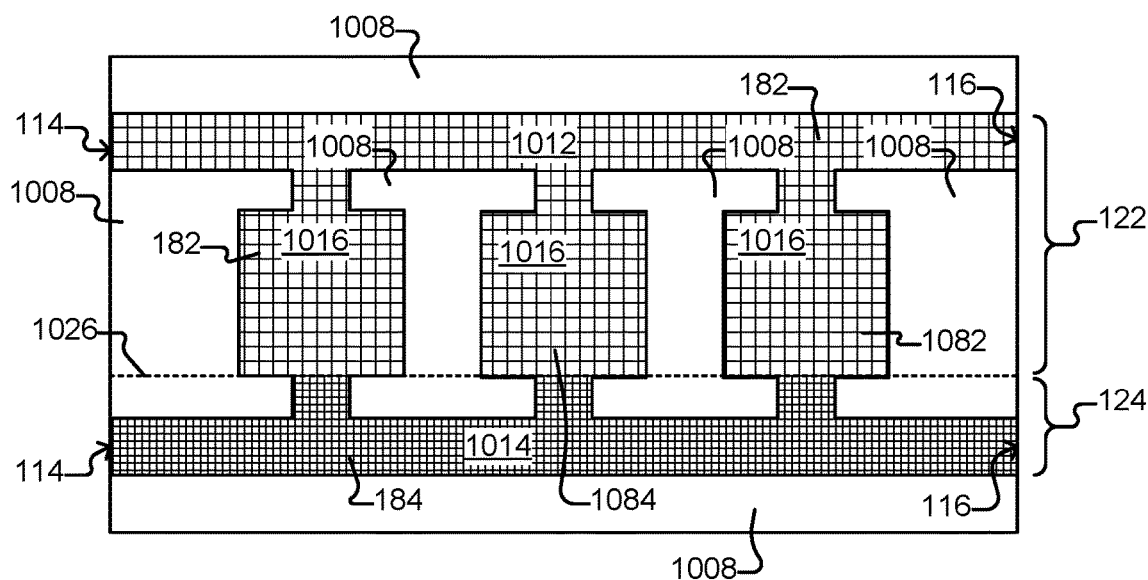
FIG. 10C is a top view of the microfluidic apparatus of FIG. 10A with the cover removed.

As mentioned, the configuration of the apparatus 100 shown in FIGS. 1A-1C as comprising a chamber 112 divided into a first chamber section 172 and a second chamber section 174 is an example, and many other configurations are possible. FIGS. 10A-10C illustrate an example of a microfluidic apparatus 1000 comprising multiple fluidic channels 1012, 1014 (two are shown but there can be more) and multiple holding pens 1016 (three are shown but there can be fewer or more) each of which can be connected to one or more of the channels 1012, 1014.

The apparatus 1000 can be generally similar to the apparatus 100, and like numbered elements in FIGS. 10A-10C can be the same as in FIGS. 1A-1C. The fluidic circuit frame 1008 of the apparatus 1000, however, can define, with the structure 104 and the cover 110, a first channel 1012, a second channel 1014, and holding pens 1016, which as shown, can be connected to the channels 1012, 1014. Otherwise, the fluidic circuit frame 1008 can be the same as or similar to the fluidic circuit frame 108.

In the example shown in FIGS. 10A-10C, the first channel 1012 and the pens 1016 can be configured to hold a first liquid medium (not shown but can be the first liquid medium 212 of FIG. 2), and the structure 104 and cover 110 can include the DEP configuration 122 for selecting and manipulating micro-objects in the first liquid medium. For example, the structure 104 can comprise the biasing electrode 156, DEP section 152, and first surface 182, and the cover 110 can comprise the biasing electrode 166, all of which can be as discussed above. Similarly, the structure 104 can also comprise the biasing electrode 158, EW section 154, dielectric layer 160, and electrowetting surface 184, and the cover 110 can also comprise the hydrophobic surface 165, layer 164, and biasing electrode 168, all of which can be as discussed above. As discussed above, the DEP configuration 122 can be for selecting and manipulating micro-objects (e.g., 228) in a first liquid medium (e.g., 212) on the first surface 182 in the first channel 1012 and pens 1016, and the EW configuration 124 can be for manipulating a liquid medium (not shown) on the electrowetting surface 184 in the second channel 1014.

In FIGS. 10A-10C, the boundary 1026 can be the same as the boundary 126 in FIGS. 1A-1C: the boundary 1026 is the boundary between the first surface 182 and the electrowetting surface 184, which can be the boundary between a first section (comparable to the first chamber section 172 of FIGS. 1A-1C) comprising the first channel 1012 and the pens 1016 and a second section (comparable to the second chamber section 174 of FIGS. 1A-1C) comprising the second channel 1014.

Although not shown in FIGS. 10A-10C or in FIGS. 8 and 9, the equipment 132 and biasing device 118 (e.g., comprising the biasing devices 202, 204 and switches 206, 208 of FIG. 2) of FIGS. 1A-1C can bias, control, and provide miscellaneous functions to the devices 800, 900, and 1000 of FIGS. 8-10C.

FIG. 11 is an example of a process 1100 for moving a micro-object from a first liquid medium in a microfluidic apparatus to a second liquid medium. For ease of illustration and discussion, the process 1100 is discussed below with respect to the apparatus 100 of FIGS. 1A-1C and the apparatus 800 of FIG. 8. The process 1100 is not so limited, however, but can be performed on other microfluidic apparatuses such as the apparatus 900 of FIG. 9, the apparatus 1000 of FIGS. 10A-10C, or other such devices.

As shown, at step 1102 of process 1100, a micro-object in a DEP configured portion of a microfluidic apparatus can be selected. FIGS. 12A-15 illustrates examples.

FIG. 12A shows a top view of the apparatus 100, with the cover 110 removed; and FIG. 12B is a across-sectional side view of the apparatus 100, corresponding to FIGS. 1C and 1B but with the first liquid medium 212 in the first chamber section 172 of the enclosure 102 and the second liquid medium 214 in the second chamber section 174 of the enclosure 102 (as illustrated in FIG. 2). In addition, micro-objects 1202 (which can be like the micro-object 218 of FIG. 2) can be suspended in the first liquid medium 212 in the first chamber section 172. FIG. 13 shows the device 800 of FIG. 8 with the first liquid medium 212 in the first section 872 of the first sub-enclosure 822 and the second liquid medium 214 in the second section 874 of the second sub-enclosure 824. Micro-objects 1202 are also shown in the first medium 212 in the first section 872.

Although not shown in FIGS. 12A-21, the equipment 132 and biasing device 118 (e.g., comprising the biasing devices 202, 204 and switches 206, 208 of FIG. 2) of FIGS. 1A-1C can bias, control, and provide miscellaneous functions to the devices 100 and 800 illustrated in FIGS. 12A-21. Indeed, the master controller 134 can be configured to perform one, some, or all of the steps of the process 1100.

Figure 14A:
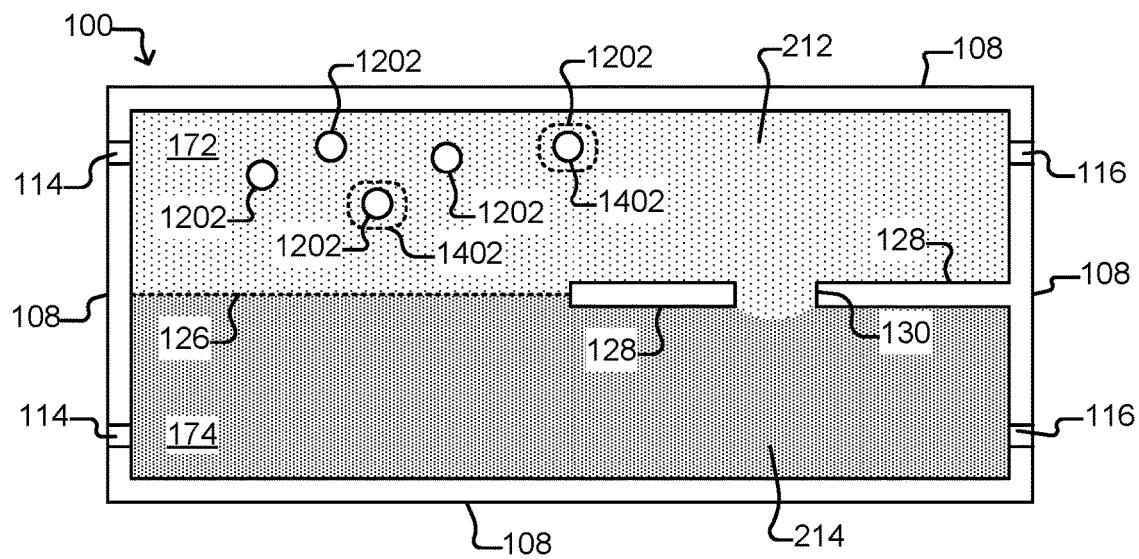
Figure 14B:
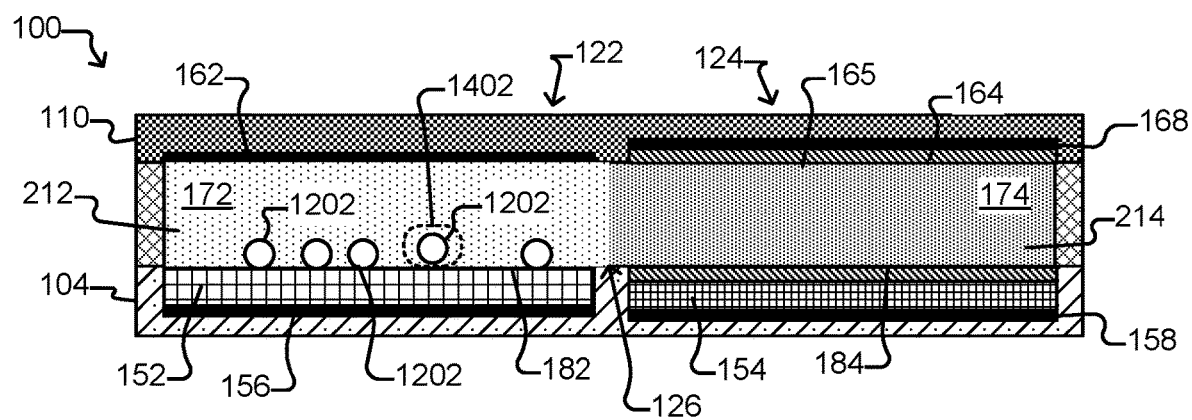
Figure 15:
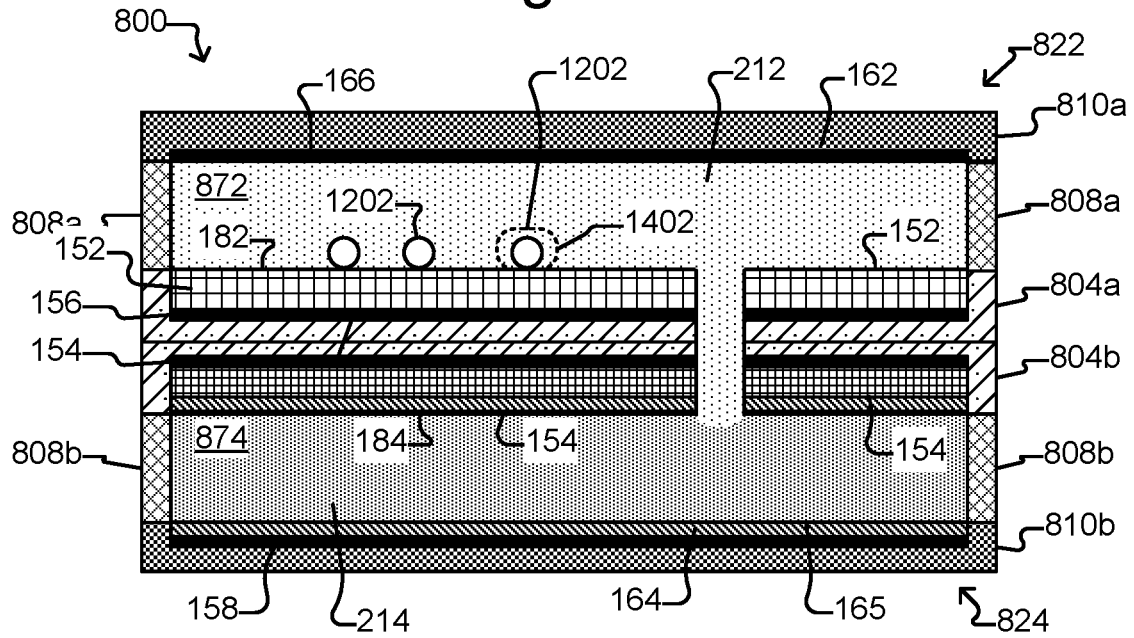

As shown in FIGS. 14A and 14B, one or more of the micro-objects 1202 in the first liquid medium 212 can be selected and captured with a DEP trap 1402. The DEP traps 1402 can be created by activating one or more DEP electrodes 222 (not shown in FIGS. 14A and 14B) at the first surface 182 of the DEP section 152 (as discussed above with respect to FIG. 2) in a pattern that surrounds the selected micro-object 1202, thereby capturing the micro-object 1202. A specific one or more of the micro-objects 1202 can be identified and selected from a group of micro-objects 1202 in the first chamber section 172 based on any of a number of characteristics (e.g., cell size and/or morphology, nuclear size and/or morphology, cell surface markers, cell secretions, and the like). Similarly, as shown in FIG. 15, one or more specific micro-objects 1202 can be identified and selected with a DEP trap 1402 in the first section 872 of the device 800.

Figure 16A:
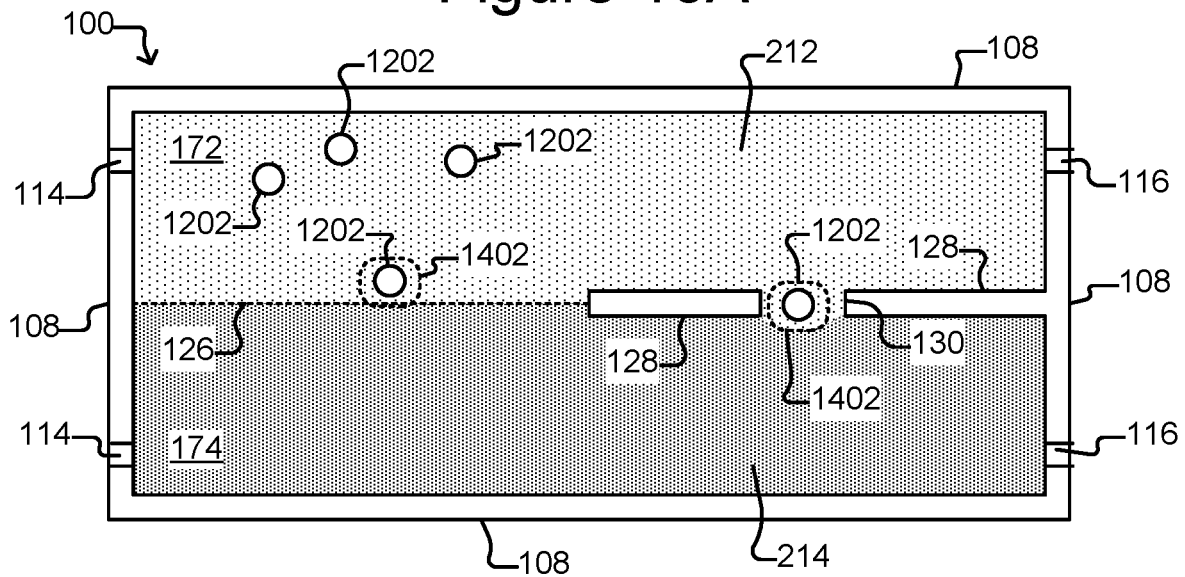
Figure 16B:
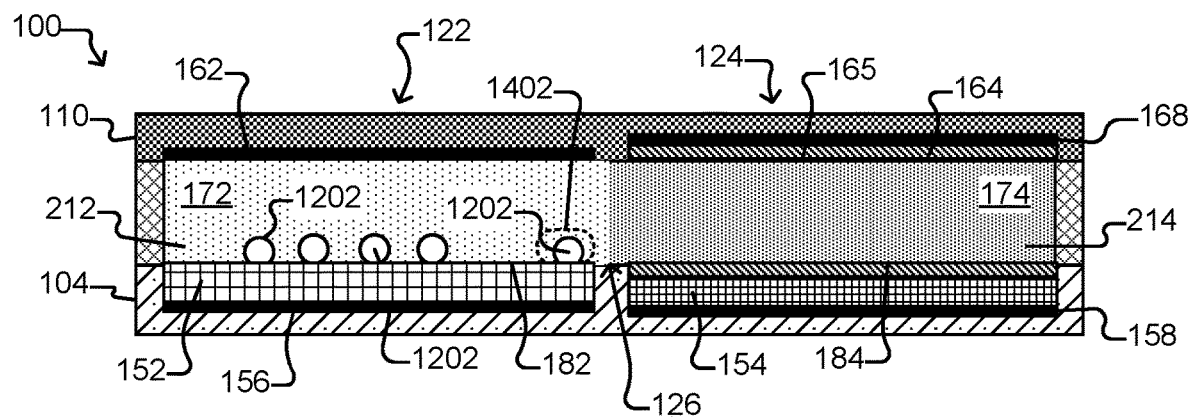
Figure 17:
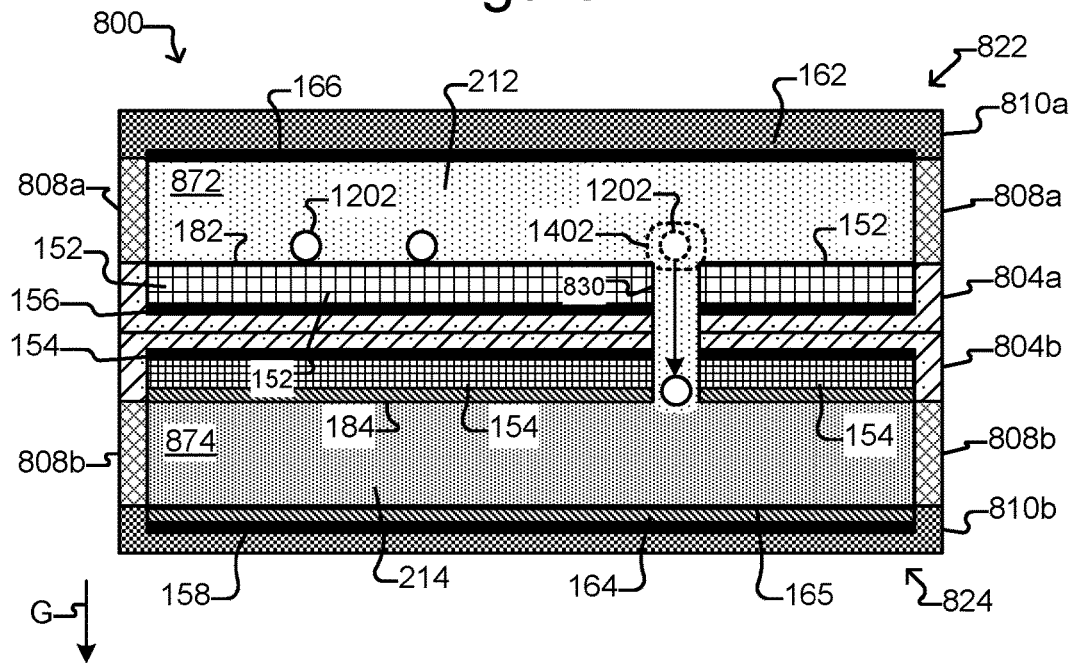

Returning again to FIG. 11, at step 1104 of process 1100, one or more micro-objects selected at step 1102 can be moved to an interface with the second liquid medium in the device. FIGS. 16A-17 illustrate examples.

As shown in FIG. 16A, a selected micro-object 1202 can be moved in the apparatus 100 to the passage 130 through the physical barrier 128. Alternatively, a selected micro-object 1202 can be moved to a portion of the boundary 126 that does not have a physical barrier. The selected micro-objects 1202 can be moved in the first liquid medium 212 in the first chamber section 172 in the apparatus 100 by moving the traps 1402, which can be accomplished by activating and deactivating DEP electrodes 222 (not shown in FIGS. 16A and 16B) on the first surface 182 of the DEP section 152 as discussed above. The movement of the selected micro-objects 1202 can involve tilting the apparatus 100 such that the force of gravity (G) pulls the micro-objects 1202 towards the boundary 126 or passage 130. In certain embodiments, the micro-objects 1202 can be moved towards the boundary 126 or passage 130 (e.g., by tilting the apparatus and allowing gravitational force to act upon the micro-objects 1202) prior to the micro-objects 1202 being selected.

As still another example illustrated in FIG. 17, a selected micro-object 1202 in the first section 872 of the device 800 can be moved to the passage 830, where the selected micro-object 1202 can be released into the passage 830. The selected micro-objects 1202 can be moved to the passage 830 by moving the trap 1402 to the passage, which can be accomplished by activating and deactivating DEP electrodes 222 (not shown in FIG. 17) on the first surface 182 of the DEP section 152, as discussed above with respect to FIG. 2. The selected micro-object 1202 can be released by deactivating DEP electrodes 222 of the trap 1402. Again, the movement of the selected micro-objects 1202 can involve tilting the apparatus 800 such that the force of gravity (G) pulls the micro-objects 1202 towards the passage 830, as discussed above.

The force of gravity (G) can move the released micro-object 1202 to the bottom of the passage 830, which is located at the interface with the second liquid medium 214 in the second section 874. Alternatively, the released micro-object 1202 can be moved down the passage 830 by forces other than gravity. For example, a flow of the first liquid medium 212 in the passage 830 can move the released micro-object 1202 down the passage 830. As another example, the micro-object 1202 can be moved down the passage 830 by the DEP trap 1402.

Figure 18A:
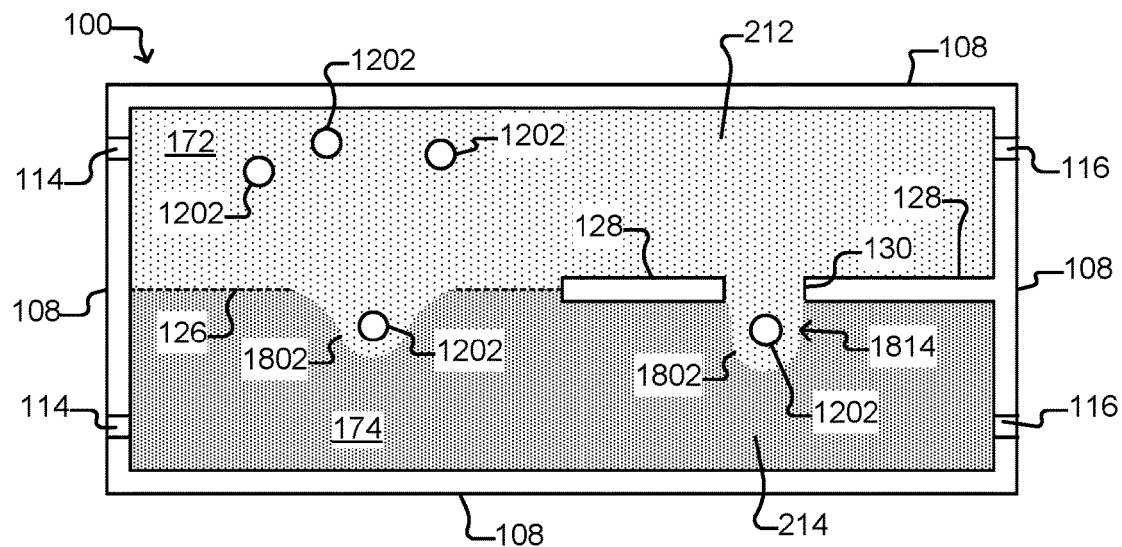

Referring again to FIG. 11, at step 1106 of process 1100, a droplet of the first liquid medium containing the micro-object from the first liquid medium 212 can be pulled into the second medium. FIGS. 18A-19 illustrate examples.

As shown in FIG. 18A, a droplet 1802 of the first liquid medium 212 with a micro-object 1202 can be pulled from the first chamber section 172, through the passage 130 in the physical barrier 128 of the apparatus 100, and into the second liquid medium 214 in the second chamber section 174 of the apparatus 100. As another example illustrated in FIGS. 18A and 18B, a droplet 1802 can be pulled into the second medium 214 from the first medium 212 across a portion of the boundary 126 where there is no physical barrier 128. Regardless, a droplet 1802 of the first liquid medium 212 can be pulled from the first chamber section 172 into the second liquid medium 214 in the second chamber section 174 by activating EW electrodes 232 (not shown in FIGS. 18A and 18B) on the electrowetting surface 184 in a region 814 adjacent the boundary 126 between the first and second liquid media 212, 214, generally as discussed above with respect to FIG. 2. As noted in the discussion of FIG. 2 above, active EW electrodes 232 on the electrowetting surface 184 can attract the first liquid medium 212 and thereby move a droplet of the first liquid medium 212 along the electrowetting surface 184. Another example is shown in FIG. 19, which shows an example of drawing a droplet 1802 of the first medium 212 from the passage 830 into the second medium 214 in the second section 874.

Additional actions can be taken to aid in pulling a droplet 1802 from the first chamber section 172 into the second chamber section 174. For example, a pressure differential can be created that tends to draw a droplet 1802 from the first chamber section 172 into the second chamber section 174. Such a pressure differential can aid in pulling the droplet 1802 into the second chamber section 874 and can thus be utilized in conjunction with activating EW electrodes 232 as discussed above. Such a pressure differential can be induced hydrodynamically, by a piezo device, utilizing air pressure, utilizing liquid pressure, or the like. Rather than aiding in pulling a droplet 1802 into the second chamber section 174, inducing a pressure differential can be utilized to pull the droplet 1802 into the second chamber section 174 without activating EW electrodes 232. Pressure and/or other techniques can thus be utilized to aid in pulling a droplet 1802 into the second chamber section 174, or such techniques can be utilized by themselves to pull a droplet 1802 into the second chamber section 174 without activating EW electrodes 232.

Figure 18B:
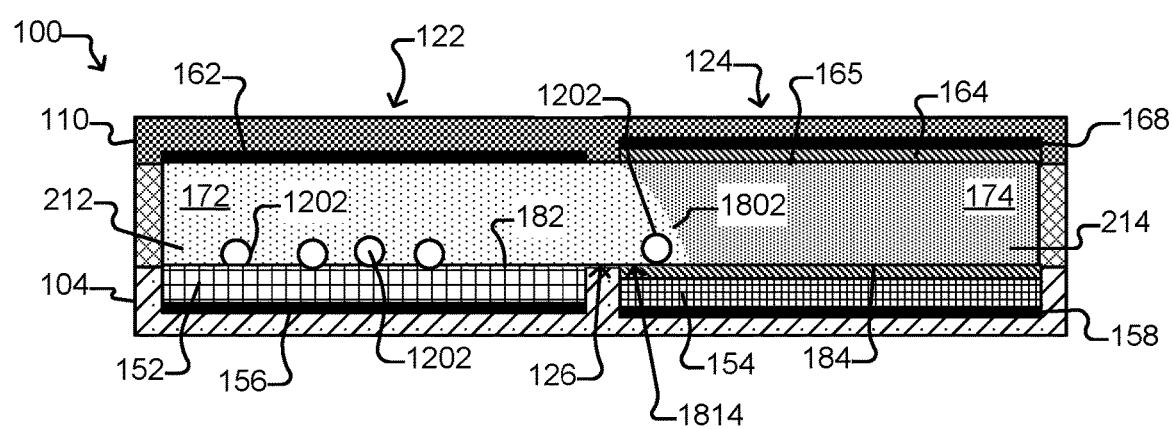
Figure 19:
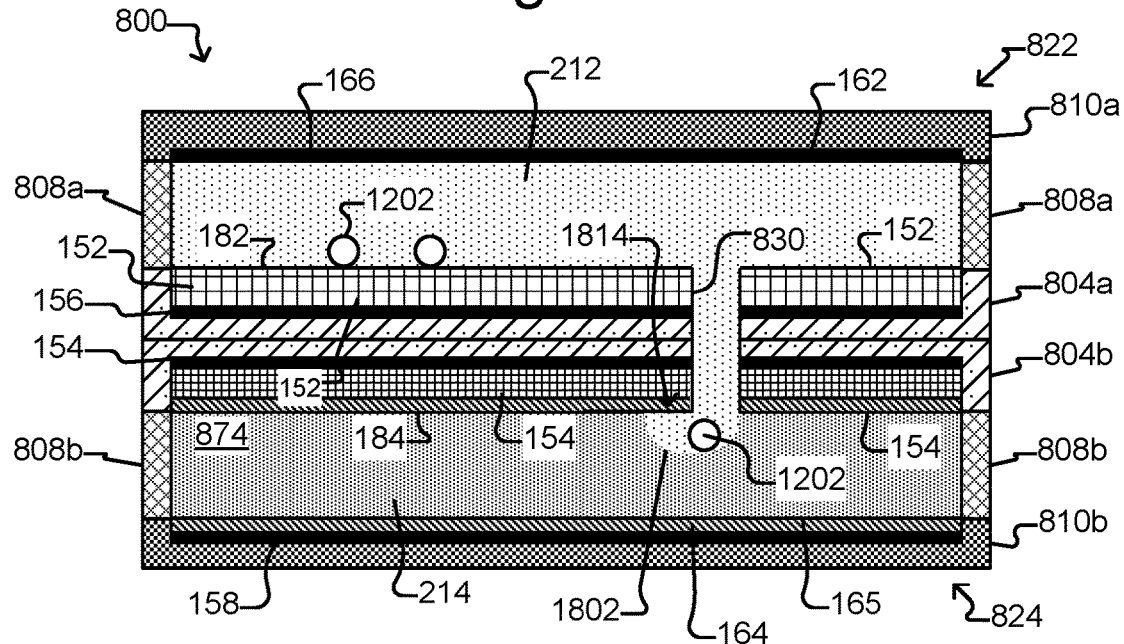

Although not shown in FIGS. 18A and 18B, additional elements can be included. For example, a moveable cutting tool (e.g., comprising a knife blade) can be provided in the chamber 112 and configured to separate a droplet 1802 in the second chamber section 174 from the medium 212 in the first chamber section 172.

Figure 20A:
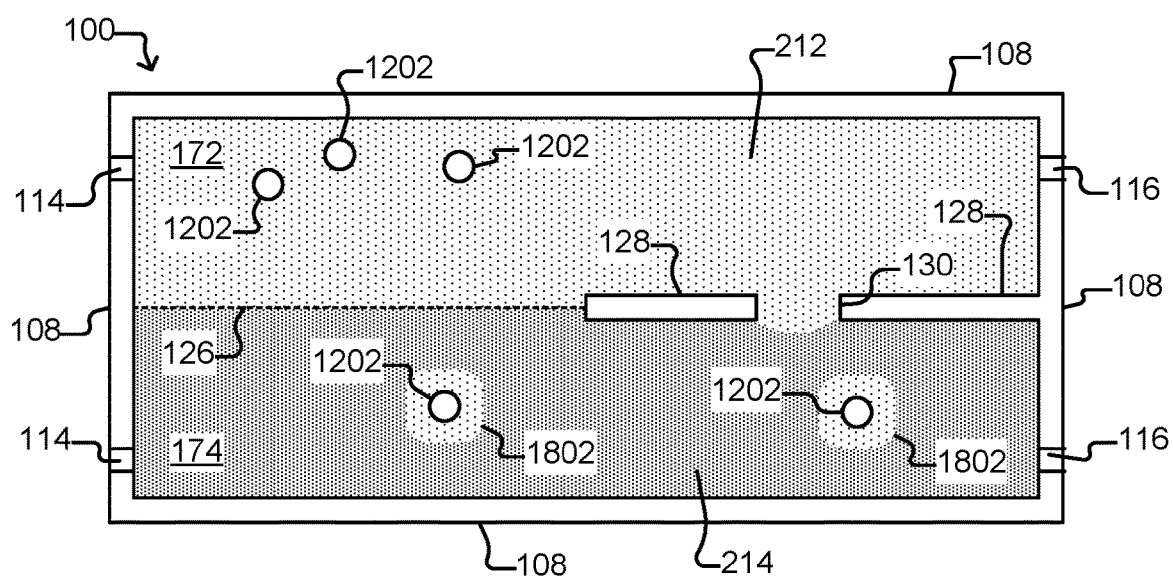
Figure 20B:
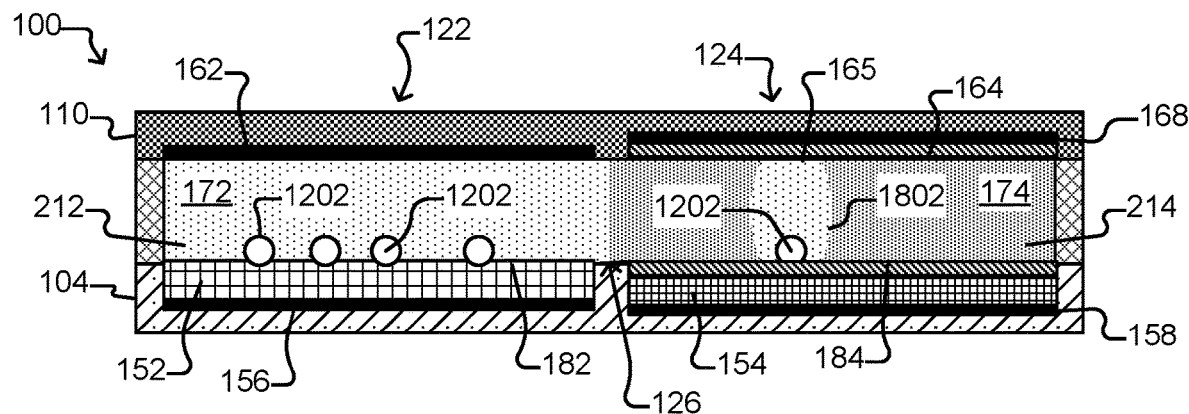
Figure 21:
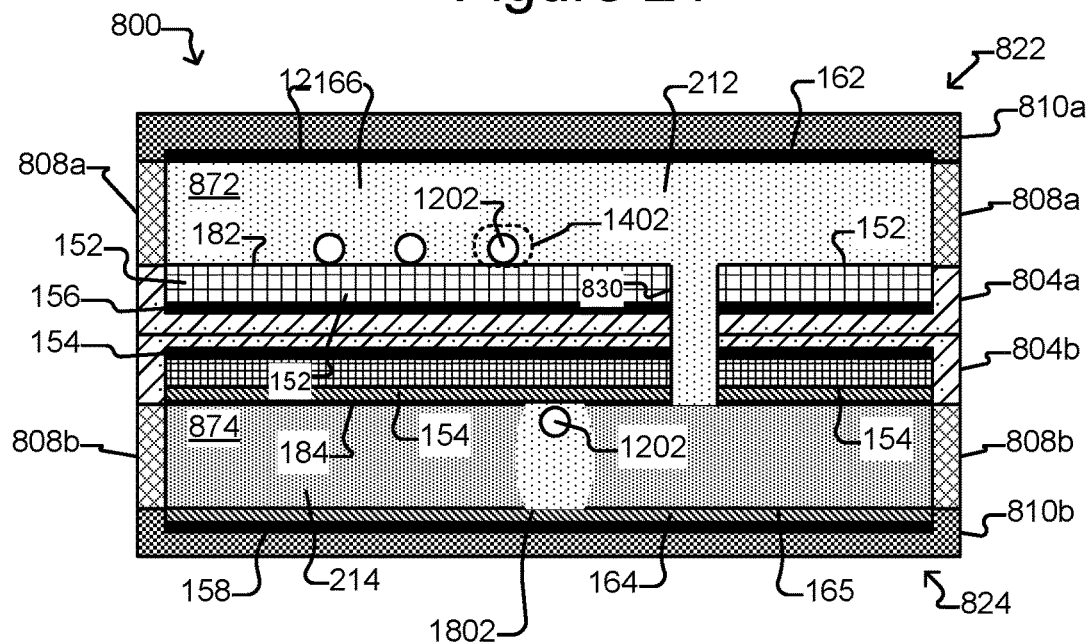

As shown in FIGS. 20A and 20B, the droplets 1802 of the first liquid medium 212 pulled into the second medium 214 can be moved about (along with the micro-objects 1202 in the droplets 1802) in the second chamber section 174, which can be done by selectively activating and deactivating EW electrodes 232 (not shown in FIGS. 20A and 20B) at a region of the electrowetting surface 184 that is immediately adjacent (e.g., in front of) the droplet 1802, generally as discussed above with respect to FIG. 2. As shown in FIG. 21, the droplets 1802 can similarly be moved about in the second liquid medium 214 in the second section 874 of apparatus 800. For example, the droplets 1802 can be moved to other locations in or exported from the microfluidic device.

FIG. 22 is an example of a process 2200 for culturing biological micro-objects in a microfluidic apparatus. For ease of illustration and discussion, the process 2200 is discussed below with respect to the apparatus 1000 of FIGS. 10A-10C. The process 2200 is not so limited, however, but can be performed with other microfluidic apparatuses.

Figure 24:
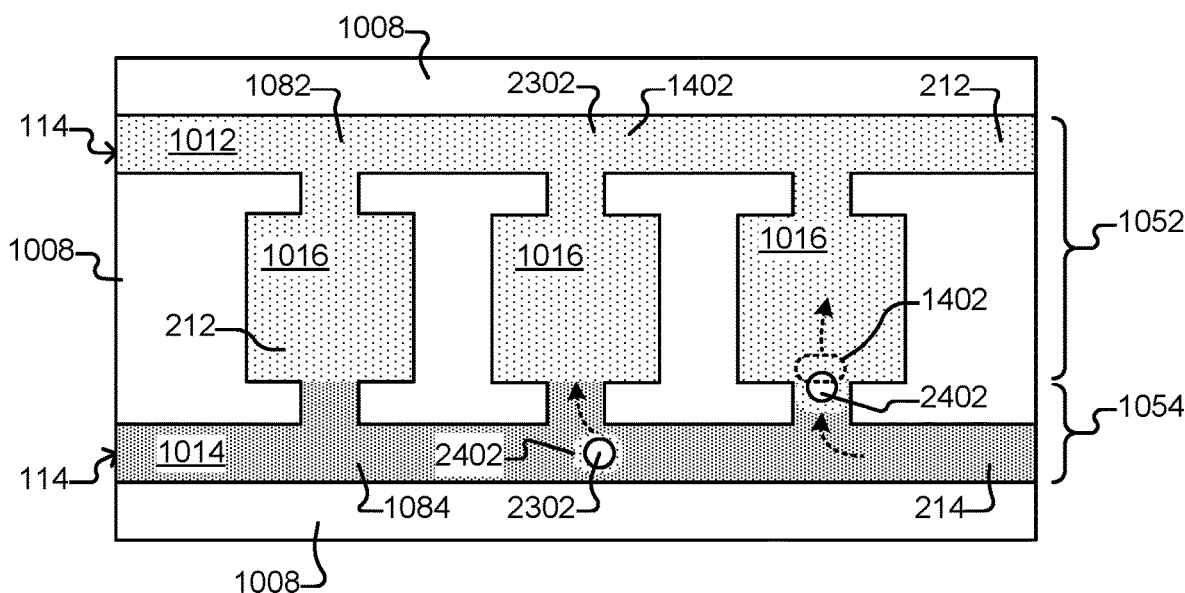
Figure 25:
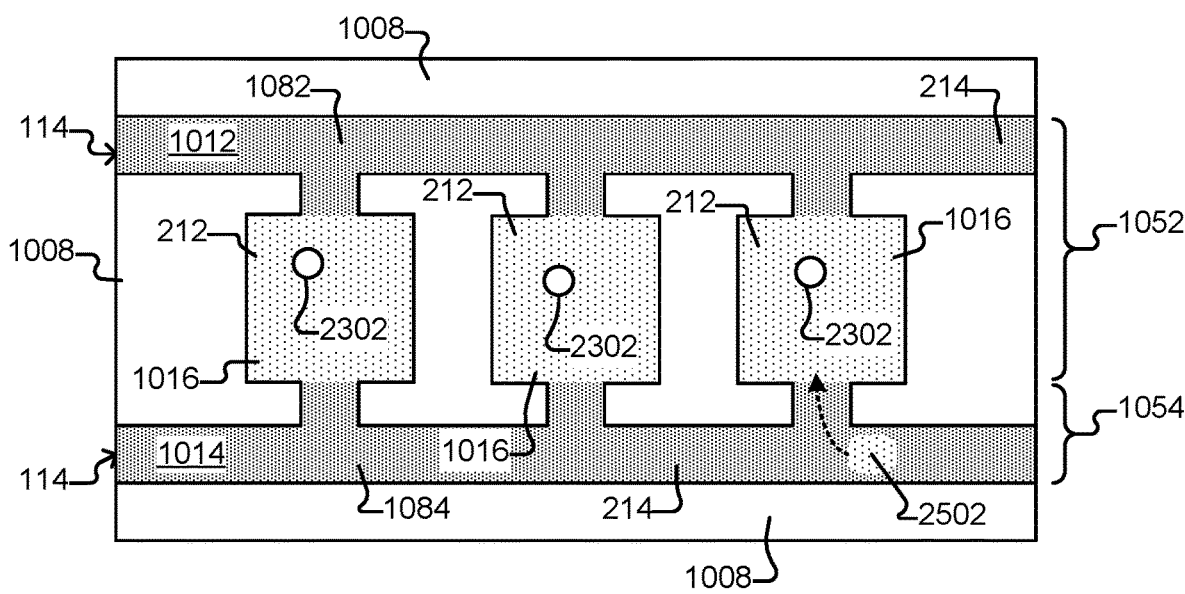

Although not shown in FIGS. 23-25, the equipment 132 and biasing device 118 (e.g., comprising the biasing devices 202, 204 and switches 206, 208 of FIG. 2) of FIGS. 1A-1C can bias, control, and provide miscellaneous functions to the apparatus 1000 illustrated in FIGS. 23-25. The master controller 134 can be configured to perform one, some, or all of the steps of the process 2200.

As shown, at step 2202 of process 2200, biological micro-objects can be loaded into holding pens in a microfluidic device. Examples are illustrated in FIGS. 23 and 24, which show top views of the apparatus 1000 of FIGS. 10A-10C, and in particular with the cover 110 removed as shown in FIG. 10C. In FIGS. 23 and 24, the first channel 1012 and the pens 1016 contain the first liquid medium 212 and the second channel 1014 contains the second liquid medium 214.

As shown in FIG. 23, biological micro-objects 2302 can be selected in the first channel 1012 and moved into the pens 1016. For example, a particular biological micro-object 2302 can be selected and moved by trapping the particular micro-object 2302 with a DEP trap 1402 and moving the DEP trap 1402 into a pen 1016, as discussed above with respect to FIG. 11. The movement of the biological micro-objects 2302 can involve tilting the apparatus 1000 such that the force of gravity (G) pulls the biological micro-objects 2302 towards and/or into the pens 1016. In certain embodiments, the biological micro-objects 2302 can be moved towards and/or into the pens 1016 (e.g., by tilting the apparatus and allowing gravitational force to act upon the biological micro-objects 2302) prior to the biological micro-objects 2302 being selected.

In the example shown in FIG. 24, biological micro-objects 2302 can be introduced (e.g., through an inlet 114) into the second channel 1014. As shown, one or more of the micro-objects 2302 can be inside droplets 2402 of a medium (e.g., the first medium 212) in the second channel 1014. Those droplets 2402 can be moved to openings of the pens 1016 generally as shown. The droplets 2402 can be moved in the second medium 214, generally as discussed above. Once a droplet 2402 is moved to an interface between the first medium 212 and the second medium 214 at an opening to a pen 1016, the one or more biological micro-objects 2302 can be moved from the droplet 2402 in the second medium 214 into the first medium 212 in the pen 1016. For example, the droplet 2402 at the interface between the first medium 212 and the second medium 214 can be merged with the interface by generating an electrowetting force at the boundary. Thereafter, DEP traps 1402 that attract a micro-object 2402 can optionally be generated in the DEP section 1052, which can thus attract a micro-object 2402 sufficiently to pull the micro-object 2402 away from the interface between the first medium 212 and the second medium 214.

Regardless of how the biological micro-objects 2302 are loaded into pens 1016 at step 2202, individual biological micro-objects 2302 can be placed into pens 1016 such that each of one or more of the pens 1016 contains a single cell. Of course, multiple biological micro-objects 2302 can be placed into one or more individual pens 1016.

As shown, at step 2204 of process 2200, the biological micro-objects 2302 in the pens 1016 can be cultured. For example, once one or more biological micro-objects 2302 are placed into each pen 1016, the micro-objects can be left for a time to grow, secrete biological material, divide, or the like. Nutrients can be provided to the biological micro-objects 2302 in the pens 1016 in a flow (not shown) of the first medium 212 in the first channel 1012. As another example, as shown in FIG. 25, once biological micro-objects 2302 are in the pens 1016, the first liquid medium 212 can be replaced in the first channel 1012 with the second liquid medium 214. This can keep the micro-objects 2302 from escaping the pens 1016 into the first channel 1012. Nutrients can be provided to the micro-objects 2302 in the pens 1016 by moving droplets 2502 of the first liquid medium 212 through the second liquid medium 214 in the second channel 1014 into the pens 1016. Such droplets 2502 can contain nutrients for the micro-objects 2302 in the pens 1016. The droplets 2502 can be moved in the second channel 1014 in the same way that droplets 1802 are moved as discussed above with respect to FIGS. 18A-21.

Figure 26:
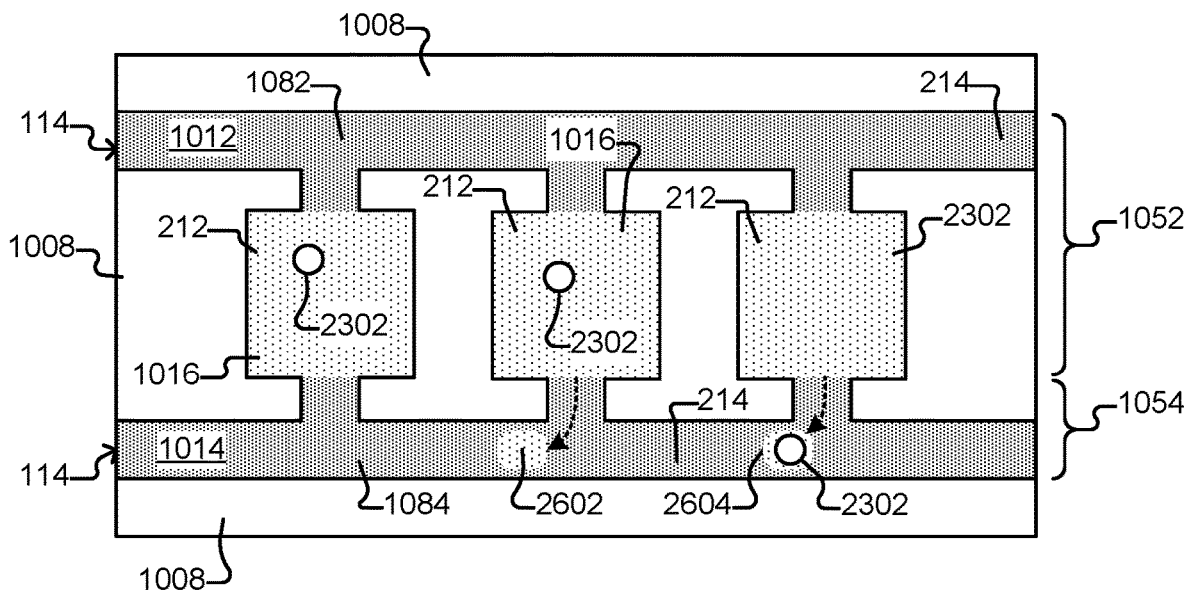

At step 2206 of process 2200, droplets of the first liquid medium can be pulled from the pens into the second channel. For example, as shown in FIG. 26, an aliquot in the form of one or more droplets 2602 of the first liquid medium 212 can be pulled from a pen 1016 into the second liquid medium 214 in the second channel 1014. Such a droplet 2602 can then be moved in the second channel 1014 to a location where the droplet 2602 can be analyzed to determine the chemical or material content of the droplet 2602. The content of the first liquid medium 212 in any of the pens 1016 can thus be analyzed by removing one or more droplets 2602 form the pen 1016. The droplet 2602 can be pulled from a pen 1016 into the second channel 1014 and moved in the second liquid medium 214 in the second channel 1014 as discussed above with respect to 20A-21.

As another example, a droplet 2604 containing a biological micro-object 2302 can be pulled from a pen 1016 into the second channel 1014. This can be accomplished in accordance with the process 1100 performed in a pen 1016 and the second channel 1014.

Figure 27:
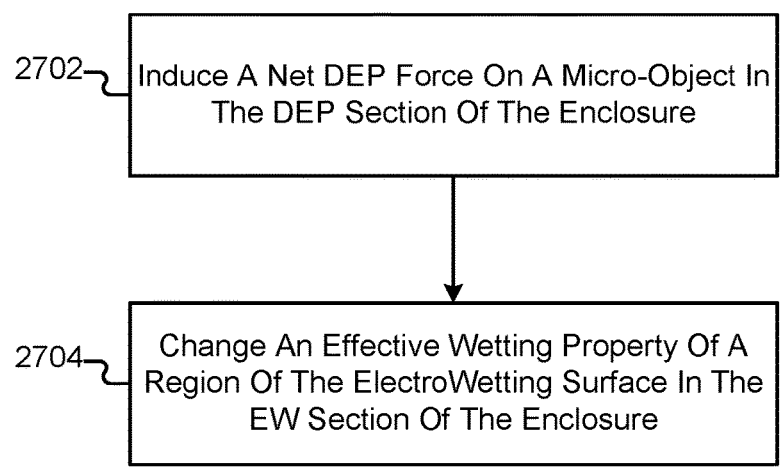
FIG. 27 shows an example of a process that can be performed on the microfluidic apparatus of FIGS. 1A-1C or the microfluidic apparatus of FIGS. 10A-10C according to some embodiments of the invention.

FIG. 27 illustrates an example of a process 2700 that can be performed on a microfluidic apparatus comprising at least one DEP section and at least one EW section. For example, the process 2700 can be performed on the microfluidic apparatus 100 of FIGS. 1A-1C or the apparatus 1000 of FIGS. 10A-10C.

As shown, at step 2702, a net DEP force can be induced on a micro-object in a DEP section of a microfluidic apparatus. For example, the net DEP force (F) can be induced on the micro-object 228 as illustrated in FIG. 2 and discussed above. The net DEP force (F) can be sufficiently strong to move the micro-object 228 on the first surface 182. Generally as discussed above, the step 2702 can be repeated for different DEP electrodes 222 at the first surface 182 to move the micro-object 228 along any of a variety of possible paths across the surface 182.

At step 2704, an effective wetting property of a region of an electrowetting surface in an EW section of the microfluidic apparatus can be changed. For example, an effective wetting property of the electrowetting surface 184 at an EW electrode 232 can be changed as illustrated in FIG. 2 and discussed above. The change can be sufficient to move liquid medium (e.g., a droplet of liquid medium) on the electrowetting surface 184. Generally as discussed above, the step 2704 can be repeated for different EW electrodes 232 at the electrowetting surface 184 to move the liquid medium (e.g., a droplet) along any of a variety of possible paths across the electrowetting surface 184.

The steps 2702 and 2704 can alternatively be performed in any manner discussed herein for inducing a net DEP force on a micro-object or changing an effective wetting property of an electrowetting surface. Moreover, the steps 2702 and 2704 can be performed simultaneously.

FIG. 28 illustrates an example of a droplet generator 2806 for providing fluidic droplets to a microfluidic circuit 2800. In the example shown in FIG. 28, the microfluidic circuit 2800 is illustrated as comprising a perfusion channel 2812, a sample channel 2814, and holding pens 2816, which can be fluidically connected to one or both of the channels 2812 and 2814. The perfusion channel 2812 and holding pens 2816 can comprise DEP configurations, and the sample channel 2814 can comprise an EW configuration. For example, the profusion channel 2812 and holding pens 2816 can be like the DEP channel 1012 and holding pens 1016 of FIGS. 10A-10C, and the sample channel 2814 can be like the EW channel 1014 of FIGS. 10A-10C. The microfluidic circuit 2800, however, is but an example, and the droplet generator 2806 can be utilized with other microfluidic circuits.

For example, the droplet generator 2806 can be utilized with microfluidic circuits that do not include DEP and/or EW configured sections. Regardless, the droplet generator 2806 and any microfluidic circuit to which it provides droplets can be part of a microfluidic device (either an integral part or connected thereto), which can be like any of the microfluidic devices illustrated in the drawings or described herein. Although one droplet generator 2806 is shown in FIG. 28, more than one such droplet generator 2806 can provide droplets to the microfluidic circuit 2800.

The perfusion channel 2812 and the pens 2816 can be filled with a first fluidic medium 2822, and the sample channel 2814 can be filled with a second fluidic medium 2824. The first fluidic medium 2822 (hereinafter an "aqueous medium") can be an aqueous medium, such as a sample medium for maintaining, culturing, or the like biological micro-objects 2830. The second fluidic medium 2824 (hereinafter an "immiscible medium") can be a medium in which the aqueous medium 2822 is immiscible. Examples of the aqueous medium 2822 and the immiscible medium 2824 include any of the examples discussed above for various media.

As shown, the droplet generator 2806 can comprise one or more fluidic inputs 2802 and 2804 (two are shown but there can be fewer or more) and a fluidic output 2808, which can be connected to the sample channel 2814. Aqueous medium 2822, immiscible medium 2824, biological micro-objects 2830, reagents, and/or other biological media can be loaded through the inputs 2802 and 2804 into the droplet generator 2806. The droplet generator 2806 can generate and output into the channel 2814 droplets 2820 of the aqueous medium 2822 (which can, but need not, contain one or more biological micro-objects 2830), reagents, or other biological medium. If the channel 2814 is configured as an EW channel, the droplets 2820 can be moved in the channel 2814 utilizing electrowetting or optoelectrowetting as discussed above. Alternatively, the droplets 2820 can be moved in the channel 2814 by other means. For example, the droplets 2820 can be moved in the channel 2814 using fluidic flow, dielectrophoresis, or the like.

The droplet generator 2806 itself can be part of an EW section (e.g., EW section 124 in the drawings of the present application) of a microfluidic device and can thus comprise an EW configuration with a photoconductive substrate (e.g., as illustrated in U.S. Pat. No. 6,958,132), a photo-actuated circuit substrate (e.g., as illustrated in U.S. Patent Application Publication No. 2014/0124370 (attorney docket no. BL9-US)), a phototransistor-based substrate (e.g., as illustrated in U.S. Pat. No. 7,956,339), or an electrically-actuated circuit substrate (e.g., as illustrated in U.S. Pat. No. 8,685,344). Alternatively, the droplet generator can have a T- or Y-shaped hydrodynamic structure (e.g., as illustrated in U.S. Pat. Nos. 7,708,949, 7,041,481 (reissued as RE41,780), 2008/0014589, 2008/0003142, 2010/0137163, and 2010/0172803). All of the foregoing U.S. patent documents (i.e., U.S. Pat. Nos. 6,958,132; 7,956,339; 8,685,344; 7,708,949; and 7,041,481 (reissued as RE41,780); and U.S. Patent Application Publication Nos. 2014/0124370; 2008/0014589, 2008/0003142, 2010/0137163, and 2010/0172803) are incorporated by reference herein in their entirety.

FIGS. 29 and 30 illustrate examples of alternative microfluidic circuits 2900 and 3000 that include holding pens 2916 and 3016, respectively, which are fluidically connected to the sample channel 2814 but not to the perfusion channel 2812. In such configurations, if the sample channel 2814 is EW configured, the holding pens 2916 and 3016 can also be EW configured. The illustrations of the microfluidic circuits 2800, 2900, and 3000 are examples only, and variations are possible. For example, holding pens 2816 need not be vertically aligned with pens 3016 in the microfluidic circuit 3000 of FIG. 30.

The droplet generator 2806 can be utilized to load biological micro-objects and/or facilitate the running of biochemical and/or molecular biological workflows on the microfluidic device. FIGS. 28-30 illustrate non-limiting examples.

As shown in FIG. 28, the droplet generator 2806 can output into the sample channel 2814 a droplet 2820 of sample material 2822 containing a micro-object 2830. The droplet 2820 can then be moved via the sample channel 2814 into one of the holding pens 2816, as shown in FIG. 28. Droplets 2820 generated by the droplet generator 2806 that do not contain a micro-object 2830 can be discarded rather than moved into a holding pen 2816.

FIGS. 29 and 30 illustrate another example in which the droplet generator 2806 generates a droplet 2920 comprising a reagent (or other biological material). The reagent-containing droplet 2920 can be moved through the sample channel 2814 and into one of the holding pens 2916 or 3016 containing the immiscible medium 2824. Prior to or after moving the reagent-containing droplet 2920 into one of the holding pens 2916 or 3016, one or more micro-objects 2930 in one or more droplets 2932 can be moved into the same holding pen 2916 or 3016. The reagent-containing droplet 2920 can then be merged with the droplet 2932 containing the micro-object 2930, allowing the reagents of droplet 2920 to mix and chemically react with the contents of droplet 2932. The one or more micro-object-containing droplets 2932 can be supplied by the droplet generator 2806, as shown in FIG. 28, or can be obtained from a holding pen 2816, as shown in FIGS. 29 and 30. The micro-object 2930 can be a biological micro-object, such as a cell, which has optionally been cultured (e.g., in a holding pen 2816) prior to being moved to the holding pen 2916 or 3016. Alternatively, the micro-object 2930 can be a bead, such as an affinity bead that is capable of binding to molecules of interest in a sample (e.g., cell secretions present in sample material 2822 after the sample material 2822 has been used to culture one or more biological cells). In still other alternatives, the one or more droplets 2932 can contain no micro-objects but only aqueous medium, such as sample material 2822, e.g., that contains cell secretions after the sample material 2822 has been used to culture one or more biological cells.

FIG. 31 illustrates an example of a process 3100 that can be performed in a microfluidic device comprising a droplet generator 2806 and microfluidic circuit like any of 2800, 2900, or 3000.

At step 3102 of the process 3100, a biological micro-object can be cultured in a holding pen filled with a sample medium (e.g., cell culture medium). For example, a micro-object 2830 of FIG. 28 or a micro-object 2930 in FIGS. 29 and 30 can be biological and can be cultured in its holding pen. Culturing can be generally as discussed above with respect to step 2204 of FIG. 22. For example, culturing can include perfusing the channel 2812 with the sample medium 2822 and/or other culturing media. Step 3102 can be performed over a specified period of time.

At step 3104, the cultured biological micro-object can be moved from the sample-medium-filled holding pen in which it was cultured to a holding pen filled with a medium in which the sample medium is immiscible. For example, the cultured micro-object 2830 or 2930 can be moved in a droplet 2820 or 2932 of sample medium 2822 from one of the holding pens 2816 into one of the holding pens 2916 or 3016, as illustrated in FIG. 29 or 30 and discussed above.

At step 3106, the cultured biological micro-object can be subjected to one or more treatments or processes in the immiscible-medium-filled holding pen. For example, one or more droplets 2920 containing one or more reagents can be produced by the droplet generator 2806 and moved into the immiscible-medium-filled holding pen 2916 or 3016 and merged with the droplet 2932 containing the cultured biological micro-object 2830, as shown in FIG. 29 or 30 and discussed above. For example, a first reagent-containing droplet 2920 can contain a lysing reagent. Merger of the droplet 3932 containing the cultured biological micro-object 2830 with the first reagent-containing droplet 2920 containing lysing reagent, would result in the lysis of the cultured biological micro-object 2830. In other words, a single new droplet (not shown) would be formed that contains a cell lysate from the cultured biological micro-object 2830. Additional (e.g., second, third, fourth, etc.) reagent-containing droplets 2920 could then be merged with the cell lysate-containing new droplet, so as to further process the cell lysate as desired.

In addition or as another example, one or more droplets containing one or more labeled capture micro-objects (not shown) having an affinity for a secretion or other material or materials of interest (e.g., nucleic acids such as DNA or RNA, proteins, metabolites, or other biological molecules) produced the cultured biological micro-object 2830 can be generated by the droplet generator 2806 and moved into the immiscible-medium-filled pen 2916 or 3016 and merged with the droplet of sample medium 2822 containing the cultured biological micro-object 2830 in a similar manner. In cases where the cultured biological micro-object 2830 has already been lysed, capture micro-object-containing droplet 2920 could contain one or more affinity beads (e.g., having affinity for nucleic acids, such as DNA, RNA, microRNAs, or the like) which, upon merger with the cell lysate-containing droplet in holding pen 2916 or 3016, could bind to target molecules present in the lysate.

At step 3108, the treated biological micro-object can be optionally processed. For example, if at step 3106, a capture object (not shown) is moved into the immiscible-medium-filled pen 2916 or 3016 with the cultured biological micro-object 2830, the pen 2916 or 3016 can be monitored at step 3108 for a reaction (e.g., a fluorescent signal) indicative of a quantity of the material of interest bound to the labeled capture micro-object. Alternatively, such a capture micro-object (not shown) can be removed (e.g., in a droplet 2922) from the pen 2916 or 3016 and exported from the microfluidic device (not shown in FIGS. 28-30) for subsequent analysis. As yet another example, the treated biological micro-object 2830 can be removed (e.g., in a droplet 2932) from the pen 2916 or 3016 and exported from the microfluidic device (not shown) for subsequent analysis.

Although specific embodiments and applications of the invention have been described in this specification, these embodiments and applications are exemplary only, and many variations are possible. For example, the method of FIG. 31 can be performed with respect to sample material contain cell secretions (e.g., after the sample material 2822 has been used to culture one or more biological cells). In such an embodiment, step 3102 would remain the same, but step 3104 would involve moving droplets 2932 which can contain no micro-objects but only aqueous medium, such as sample material 2822 containing cell secretions, into immiscible-medium-containing holding pens 2916 or 3016, and steps 3106 and 3108 would be performed with respect to such aqueous medium-containing droplets 2932. Furthermore, the DEP configurations (e.g., 122) illustrated in the drawings or described herein are examples. Generally speaking, the DEP configurations (e.g., 122) can be any type of optoelectronic tweezers (OET) device known in the art, examples of which are disclosed in U.S. Pat. No. 7,612,355 (now RE44,711), U.S. Pat. No. 7,956,339, and U.S. Patent Application Publication No. 2014/0124370. Other examples of the DEP configurations include any kind of electronically controlled electronic tweezers, an example of which is disclosed in U.S. Pat. No. 6,942,776. Generally speaking, the EW configurations can be any type of optoelectronic wetting (OEW) devices known in the art, examples of which are disclosed in U.S. Pat. No. 6,958,132. Other examples of EW configurations include electrowetting on dielectric (EWOD) devices, which can be electronically controlled, an example of which is disclosed in U.S. Pat. No. 8,685,344. All of the foregoing US patent documents (U.S. Pat. No. 7,612,355 (now RE44,711); U.S. Pat. No. 7,956,339; U.S. Patent Application Publication No. 2014/0124370; U.S. Pat. No. 6,942,776; U.S. Pat. No. 6,958,132; and U.S. Pat. No. 8,685,344) are incorporated herein in their entirety by reference.

We claim:

1. A microfluidic apparatus, comprising:
an enclosure configured to hold a first liquid medium disposed on a first surface in a first section of said enclosure and a second liquid medium disposed on an electrowetting surface in a second section of said enclosure, wherein said enclosure comprises:
a first microfluidic channel in the first section of said enclosure;
a second microfluidic channel in the second section of said enclosure;
holding pens, each holding pen connected to said first microfluidic channel and/or said second microfluidic channel; and
a boundary comprising a physical barrier located in said enclosure between said first section and said second section of said enclosure;
wherein:
said first section of said enclosure comprises a DEP configuration comprising a first biasing electrode disposed on one side of said first section of said enclosure, a second biasing electrode disposed on an opposite side of said first section of said enclosure, and a first electrode activation substrate disposed between said first surface and said first biasing electrode, wherein said first electrode activation substrate does not include a dielectric hydrophobic material, wherein said DEP configuration is configured to induce selectively net dielectrophoresis (DEP) forces in said first liquid medium sufficiently to capture and move, relative to said first surface, micro-objects in said first liquid medium in said first section of said enclosure while connected to a biasing device, and
said second section of said enclosure comprises an electrowetting (EW) configuration configured to change selectively an effective wetting characteristic of regions of said electrowetting surface sufficiently to move a liquid droplet within said second medium in said second section of said enclosure while connected to a biasing device.

2. The apparatus of claim 1, wherein said boundary further comprises a passage from said first section of said enclosure through said barrier to said second section of said enclosure.

3. The apparatus of claim 1, wherein at least part of said boundary lacks a physical barrier between said first section of said enclosure and said second section of said enclosure.

4. The apparatus of claim 1, wherein said second section of said enclosure comprises:
a first biasing electrode disposed on one side of said enclosure;
a dielectric hydrophobic material disposed on an opposite side of said enclosure, a second biasing electrode disposed on said opposite side of said enclosure; and
an electrode activation substrate disposed between said dielectric hydrophobic material and said second biasing electrode.

5. The apparatus of claim 4, wherein at least one of said first electrode activation substrate and said second electrode activation substrate comprises a photoconductive material.

6. The apparatus of claim 4, wherein said dielectric hydrophobic material is part of said EW configuration, and said dielectric hydrophobic material is less than ten nanometers thick.

7. The apparatus of claim 1, wherein said first surface and said electrowetting surface are disposed substantially in a same plane in said enclosure.

8. The apparatus of claim 1, further comprising a droplet generator configured to selectively provide droplets of one or more media into said second microfluidic channel.

9. The apparatus of claim 1, wherein said droplet generator is further configured to provide at least one of:
a droplet of a sample medium containing a micro-object; or a droplet of a reagent.

10. The apparatus of claim 1, wherein said first section of said enclosure further comprises said holding pens.

11. The apparatus of claim 1, wherein at least one of said holding pens is an isolation chamber that contains an isolation region.

12. A process of moving a droplet in a microfluidic apparatus containing:
an enclosure configured to hold a first liquid medium disposed on a first surface in a first section of said enclosure and a second liquid medium disposed on an electrowetting surface in a second section of said enclosure, wherein said enclosure comprises:
a first microfluidic channel in the first section of said enclosure;
a second microfluidic channel in the second section of said enclosure;
holding pens, each holding pen connected to said first microfluidic channel and/or said second microfluidic channel; and
a boundary comprising a physical barrier located in said enclosure between said first section and said second section of said enclosure;
wherein said first section of said enclosure comprises a DEP configuration comprising a first biasing electrode disposed on one side of said first section of said enclosure, a second biasing electrode disposed on an opposite side of said first section of said enclosure, and a first electrode activation substrate disposed between said first surface and said first biasing electrode, wherein said first electrode activation substrate does not include a dielectric hydrophobic material, wherein said DEP configuration is configured to induce selectively net dielectrophoresis (DEP) forces in said first liquid medium sufficiently to capture and move, relative to said first surface, micro-objects in said first liquid medium in said first section of said enclosure while connected to a biasing device, and said second section of said enclosure comprises an electrowetting (EW) configuration configured to change selectively an effective wetting characteristic of regions of said electrowetting surface sufficiently to move a liquid droplet within said second liquid medium in said second section of said enclosure while connected to a biasing device,
the process comprising drawing a droplet of a first liquid medium disposed on said first surface in a first section of said enclosure into a second liquid medium disposed on said electrowetting surface in a second section of said enclosure, thereby changing an effective electrowetting characteristic of a region of said electrowetting surface at a boundary with said first surface to induce a sufficient force at said region on said droplet to draw said droplet across said boundary and into said second liquid medium.

13. The process of claim 12, wherein said droplet comprises a micro-object.

14. The process of claim 13, further comprising selecting said micro-object from a plurality of micro-objects in said first liquid medium.

15. The process of claim 14, further comprising moving said selected micro-object in said first liquid medium to said boundary adjacent said region of said electrowetting surface.

16. The process of claim 15, wherein said selecting comprises activating dielectrophoresis (DEP) electrodes at said first surface of said enclosure to create a net DEP force sufficient to capture said selected micro-object, and said moving comprises further activating and deactivating DEP electrodes at said first surface to move said selected micro-object to said boundary adjacent said region of said electrowetting surface.

17. The process of claim 16, wherein said region of said electrowetting surface is adjacent a passage through said physical barrier at said boundary, and said changing comprises drawing said droplet of said first medium through said passage into said second medium.

18. The process of claim 12, wherein said changing comprises activating EW electrodes at said region of said electrowetting surface.

19. The process of claim 18, wherein activating said EW electrodes at said region of said electrowetting surface comprises directing a pattern of light onto said region of said electrowetting surface.

20. The process of claim 12, wherein said first surface of said enclosure and said electrowetting surface are located substantially in a same plane.

21. The process of claim 12, wherein said first liquid medium is an aqueous medium and said second liquid medium is immiscible in said aqueous medium.

22. The process of claim 12, wherein said droplet comprises one of said biological micro-objects from one of said holding pens, and said drawing comprises drawing said droplet from said one of said holding pens into said second channel.

23. The process of claim 12, further comprising:
moving said biological micro-objects from said first liquid medium in said first channel into said holding pens; and
replacing said first liquid medium in said first channel with said second liquid medium.

24. The process of claim 12, further comprising:
moving one of said micro-objects in a droplet of said first liquid medium through said second liquid medium in said second channel to an interface between said first liquid medium and said second liquid medium at an opening to one of said holding pens; and
moving said one of said micro-objects from said droplet into said first liquid medium in said one of said holding pens.

25. The process of claim 12, wherein at least one of said holding pens is an isolation chamber that contains an isolation region.

* * * * *